United States Patent
Kobayashi et al.

(10) Patent No.: US 8,466,960 B2
(45) Date of Patent: Jun. 18, 2013

(54) LIQUID DROPLET RECOGNITION APPARATUS, RAINDROP RECOGNITION APPARATUS, AND ON-VEHICLE MONITORING APPARATUS

(75) Inventors: Masanori Kobayashi, Kanagawa (JP); Hideaki Hirai, Kanagawa (JP); Shin Aoki, Kanagawa (JP); Shigeru Oouchida, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 694 days.

(21) Appl. No.: 12/693,864

(22) Filed: Jan. 26, 2010

(65) Prior Publication Data
US 2010/0208060 A1  Aug. 19, 2010

(30) Foreign Application Priority Data

Feb. 16, 2009 (JP) .................... 2009-032161
Mar. 6, 2009 (JP) .................... 2009-052761
Sep. 4, 2009 (JP) .................... 2009-204319

(51) Int. Cl.
*H04N 7/18* (2006.01)
(52) U.S. Cl.
USPC ......................................................... 348/135
(58) Field of Classification Search
USPC .................. 348/135, 143, 148; 250/208.01
IPC ........................................................ H04N 7/18
See application file for complete search history.

(56) References Cited

U.S. PATENT DOCUMENTS

| | | | |
|---|---|---|---|
| 5,307,136 A * | 4/1994 | Saneyoshi | 356/3.14 |
| 6,313,454 B1 * | 11/2001 | Bos et al. | 250/208.1 |
| RE37,610 E * | 3/2002 | Tsuchiya et al. | 340/435 |
| 6,580,385 B1 * | 6/2003 | Winner et al. | 342/70 |
| 2007/0115357 A1 * | 5/2007 | Stein et al. | 348/148 |

FOREIGN PATENT DOCUMENTS

| | | |
|---|---|---|
| EP | 0 628 787 A2 | 12/1994 |
| JP | 7-198357 | 8/1995 |
| JP | 10-332576 | 12/1998 |
| JP | 2004-168304 | 6/2004 |
| JP | 2005-3666 | 1/2005 |

(Continued)

OTHER PUBLICATIONS

Shinichi Kato et al., "Development of a Rain-Light Sensor" Technical Review 2008 No. 20 of Mitsubishi Motors Corporation.
Office Action issued Mar. 8, 2013 in Japanese Patent Application No. 2009-052761 filed Mar. 6, 2009.

*Primary Examiner* — Tung Vo
(74) *Attorney, Agent, or Firm* — Oblon, Spivak, McClelland, Maier & Neustadt, L.L.P.

(57) ABSTRACT

Disclosed is a liquid droplet recognition apparatus for detecting liquid droplets attached to a front surface of a transparent member. The apparatus includes an image pickup apparatus that picks up a vertically polarized light image and a horizontally polarized light image at the front surface of the transparent member from a side of a rear surface of the transparent member; and a signal processing unit that determines whether the liquid droplets are attached to the front surface of the transparent member based on a polarized-light image ratio composed of the vertically polarized light image and the horizontally polarized light image picked up by the image pickup apparatus.

10 Claims, 28 Drawing Sheets

FOREIGN PATENT DOCUMENTS

| | | |
|---|---|---|
| JP | 2005-114704 | 4/2005 |
| JP | 2005-531752 | 10/2005 |
| JP | 2006-58122 | 3/2006 |
| JP | 2006-292543 | 10/2006 |
| JP | 4157790 | 7/2008 |
| WO | WO 03/097420 A1 | 11/2003 |
| WO | WO 2004/106857 A1 | 12/2004 |
| WO | WO 2004/106858 A1 | 12/2004 |

* cited by examiner

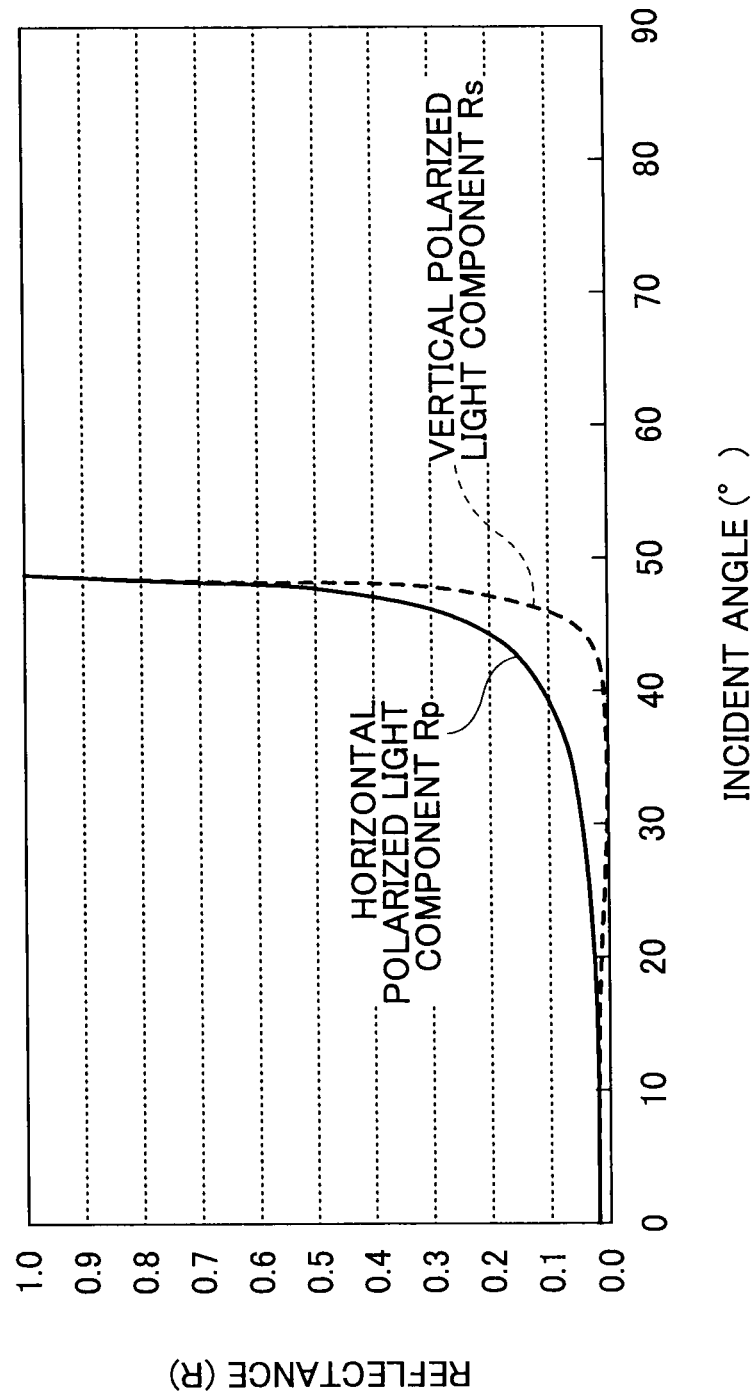

LIQUID DROPLET RECOGNITION APPARATUS, RAINDROP RECOGNITION APPARATUS, AND ON-VEHICLE MONITORING APPARATUS

BACKGROUND OF THE INVENTION

1. Field of the Invention

The present invention relates to a liquid droplet recognition apparatus that detects liquid droplets attached to the front surface of a transparent member; a raindrop recognition apparatus that detects liquid droplets such as raindrops attached to a transparent member, for example, the windshield of a vehicle or the like; and an on-vehicle monitoring apparatus.

2. Description of the Related Art

For example, Patent Documents 1 through 3 disclose apparatuses that detect the state of rainfall to drive and control a wiper of a vehicle. A raindrop detection apparatus disclosed in Patent Document 1 is provided inside a vehicle, and picks up an image outside the vehicle through a windshield with an image pickup apparatus configured to have an infinite focal distance. This apparatus determines the presence or absence of rainfall in accordance with variations in the brightness level of pixels of picked-up image information from an average value.

A raindrop detection apparatus disclosed in Patent Document 2 is provided inside a vehicle, and has an image pickup apparatus and a light source that irradiates an image-pickup region of a windshield with light. This apparatus determines whether raindrops are attached to the windshield by comparing the brightness value of an image picked up by the image pickup apparatus when the light source is turned on with that of an image picked up by the image pickup apparatus when the light source is turned off.

When raindrops are detected only with the brightness information of a picked-up image as shown in Patent Documents 1 and 2, such apparatuses are susceptible to external scattering light from both the outside and inside of the vehicle while the vehicle is running, which results in lack of reliability of raindrop detection.

A raindrop sensor disclosed in Patent Document 3 detects raindrops attached to the front surface of a windshield with a stereo camera that observes a front side through the windshield. The stereo camera is composed of a stereo optical system that generates a subject image as seen from different points of view; an image pickup apparatus that generates stereo image data based on the subject image generated by the stereo optical system; and a detection unit that detects raindrops attached to the windshield based on the generated stereo image data. This camera detects the amount of raindrops according to a principle in which the scattering of light causes a change in light amount when the raindrops are attached to the windshield.

However, the raindrop sensor using the brightness information of an image picked up by this camera often malfunctions due to surrounding brightness as a disturbance. Therefore, the raindrop sensor may determine rainfall even if it is not actually raining and cause a wiper to automatically operate.

To solve this problem, a raindrop sensor disclosed in Non-Patent Document 1 is configured to arrange a LED serving as a light source and a photodiode serving as a light-receiving part such that light from the LED is totally reflected by the front surface of a windshield to be incident on the photodiode. That is, infrared light is emitted from the LED to the windshield, and light reflected by the front surface of the windshield is received at the photodiode. This raindrop sensor determines the presence or absence of raindrops based on an output of the photodiode because the light reflected by the front surface of the windshield becomes weak when the windshield gets wetted by rain. With this raindrop sensor, the light from the LED is totally reflected by the windshield when it does not rain. Therefore, an output of the photodiode is strong enough to resist a disturbance. Thus, since this raindrop sensor simply detects raindrops based on the intensity of light rather than brightness information, reliable detection of the raindrop can be ensured.

However, since this raindrop sensor must have a particular kind of lens structure in an image-pickup optical system to provide high detection sensitivity up to a detection range boundary, high manufacturing costs are inevitable. In addition, since this raindrop sensor is dedicated to detecting raindrops, it cannot be shared with other distance sensors or the like. This results in an increase in the number of sensors to be installed in a vehicle and requires a large installation space. Presently, many sensors, such as a sensor that automatically turns on and off lights, a lane deviation preventing sensor, a sensor that automatically switches high and low beams, and a sign recognition sensor, are installed in a vehicle, which in turn causes problems in reducing manufacturing costs and saving space for installing the sensors.

Patent Document 1: JP-A-2006-292543
Patent Document 2: JP-A-2005-531752
Patent Document 3: WO2004/106858
Non-Patent Document 1: Technical Review 2008 No. 20 of Mitsubishi Motors Corporation

SUMMARY OF THE INVENTION

The present invention has been made in order to solve the above problems and may provide a liquid droplet recognition apparatus and a raindrop recognition apparatus, which are capable of reliably detecting liquid droplets attached to the front surface of a transparent member without being influenced by external scattering light under a simple configuration, and being downsized and easily installed in a vehicle such as an automobile to detect liquid droplets such as raindrops attached to the windshield of the vehicle while the vehicle is moving. In addition, the present invention may provide an on-vehicle monitoring apparatus that detects raindrops attached to the windshield of the vehicle and has the function of measuring the distance between the own vehicle and an ahead vehicle or the like.

According to a first aspect of the present invention, there is provided a liquid droplet recognition apparatus for detecting liquid droplets attached to a front surface of a transparent member. The apparatus includes an image pickup apparatus that picks up a vertically polarized light image and a horizontally polarized light image at the front surface of the transparent member from a side of a rear surface of the transparent member; and a signal processing unit that determines whether the liquid droplets are attached to the front surface of the transparent member based on a polarized-light image ratio composed of the vertically polarized light image and the horizontally polarized light image picked up by the image pickup apparatus.

According to a second aspect of the present invention, there is provided a raindrop recognition apparatus using the liquid droplet recognition apparatus described above. In the raindrop recognition apparatus, the image pickup apparatus is provided inside a vehicle and detects raindrops attached to a front surface of a windshield of the vehicle.

According to a third aspect of the present invention, there is provided an on-vehicle monitoring apparatus including a light source, a pair of image pickup apparatuses, and a signal processing unit. The light source, the pair of image pickup apparatuses, and the signal processing unit are mounted on a vehicle. In the on-vehicle monitoring apparatus, the light source irradiates a windshield of the vehicle with parallel light flux at an incident angle of Brewster's angle, one of the pair of image pickup apparatuses picks up an S-polarized light image and a P-polarized light image by receiving reflection light of the light flux irradiated from the light source to the windshield while picking up an image of a subject ahead of the vehicle, the other of the pair of image pickup apparatuses picks up an image of the subject ahead of the vehicle, and the signal processing unit has a raindrop detection processing unit and an external information processing unit, the raindrop detection processing unit determining whether raindrops are attached to the windshield based on a reflectance difference between the S-polarized light image and the P-polarized light image picked up by the one of the image pickup apparatuses and the external information processing unit calculating a distance to the subject based on the images of the subject ahead of the vehicle picked up by the one of the pair of image pickup apparatuses and the other of the pair of image pickup apparatuses.

Other objects, features and advantages of the present invention will become more apparent from the following detailed description when read in conjunction with the accompanying drawings.

BRIEF DESCRIPTION OF THE DRAWINGS

FIGS. 7A and 7B are graphs showing characteristics of variations in reflectance of a horizontally polarized light component and a vertically polarized light component with respect to an incident angle of light at the interface of a liquid droplet;

DETAILED DESCRIPTION OF THE PREFERRED EMBODIMENTS (First Embodiment)

Figure 1:
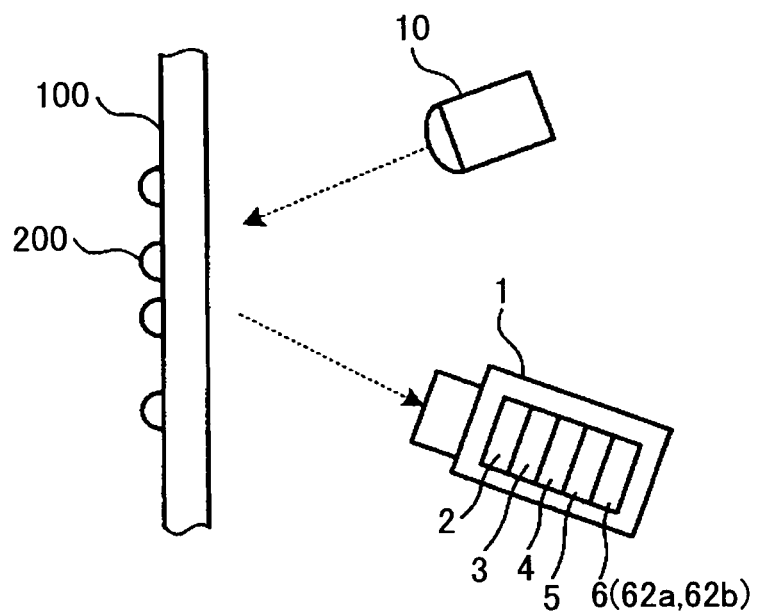
FIG. 1 is a configuration diagram of an optical system of a liquid droplet recognition apparatus according to a first embodiment of the present invention.
Figure 2:
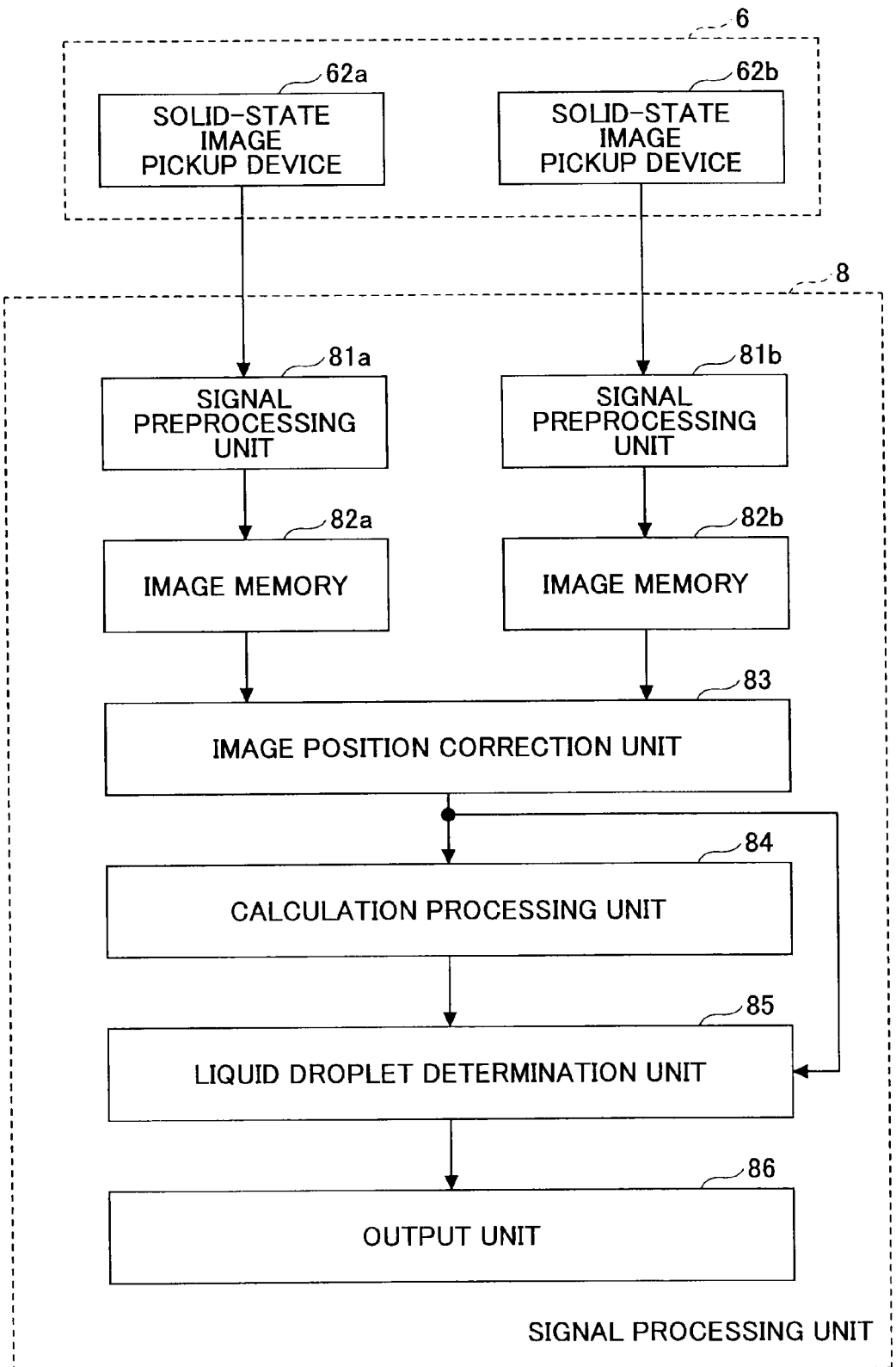
FIG. 2 is a block diagram showing the configuration of a first signal processing unit of the liquid droplet recognition apparatus according to the first embodiment of the present invention.
Figure 3:
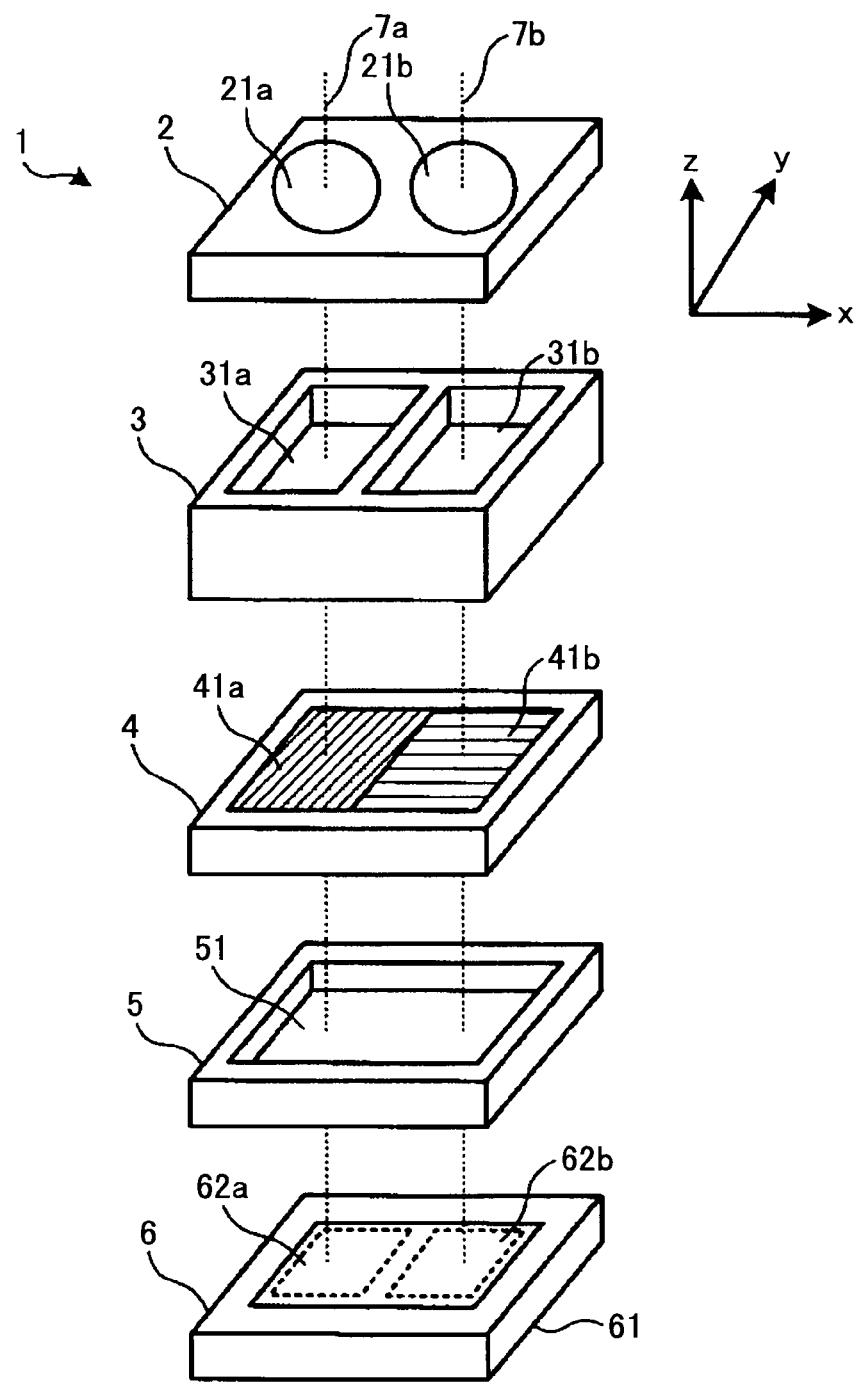
FIG. 3 is an exploded perspective view showing the configuration of a first image pickup apparatus.

FIGS. 1 and 2 show the configuration of a liquid droplet recognition apparatus according to a first embodiment of the present invention, wherein FIG. 1 is a configuration diagram of an optical system and FIG. 2 is a block diagram of a signal processing unit. As shown in FIG. 1, the optical system of the liquid droplet recognition apparatus is composed of a light source 10 and an image pickup apparatus 1 having a solid-state image pickup unit 6 provided with a solid-state image pickup device 62$a$ for picking up a vertically polarized light image and a solid-state image pickup device 62$b$ for picking up a horizontally polarized light image. With this optical system, the liquid droplet recognition apparatus picks up the vertically polarized light image and the horizontally polarized light image of liquid droplets 200 having a convex spherical surface that is attached to the front surface of a transparent screen 100. As described below, a vertical direction and a horizontal direction are the longitudinal direction and the lateral direction, respectively, of a pickup image. An exploded perspective view in FIG. 3 shows a configuration example of the image pickup apparatus 1 in which a lens array 2, a light-shielding spacer 3, a polarized light filter 4, a spacer 5, and the solid-state image pickup unit 6 are laminated together.

The lens array 2 has two image pickup lenses 21$a$ and 21$b$. The two image pickup lenses 21$a$ and 21$b$ are separate identical single lenses such as nonspherical lenses and arranged on the same plane with their light axes 7$a$ and 7$b$ parallel to each other. Here, assuming that a direction parallel to the light axes 7$a$ and 7$b$ of the image pickup lenses 21$a$ and 21$b$ is defined as a Z-axis, one direction perpendicular to the Z-axis is defined as an X-axis, and a direction perpendicular to the Z-axis and the X-axis is defined as a Y-axis, the image pickup lenses 21a and 21b are arranged on the same XY-plane.

The light-shielding spacer 3 has two opening parts 31a and 31b and is provided on the side opposite to the side of a subject through the lens array 2. The two opening parts 31a and 31b are penetrated (recessed) by a predetermined amount about the light axes 7a and 7b, respectively. Furthermore, the inner wall surfaces of the two opening parts 31a and 31b are, for example, painted black, roughened, or frosted for antireflective treatment.

The polarized light filter 4 has two polarizer regions 41a and 41b having polarized light planes different by 90° and is provided on the side opposite to the side of the lens array 2 through the light-shielding spacer 3. The two polarizer regions 41a and 41b are parallel to the XY-plane about the light axes 7a and 7b, respectively. The polarizer regions 41a and 41b convert nonpolarized light having an electromagnetic field vibrating in unspecified directions into linearly polarized light by allowing only oscillating components in directions along the polarized light planes to pass through.

The spacer 5 is formed into a rectangular frame shape having an opening part 51 penetrated corresponding to the polarizer regions 41a and 41b of the polarized light filter 4, and is provided on the side opposite to the side of the light-shielding space 3 through the polarized light filter 4.

The solid-state image pickup unit 6 has the two solid-state image pickup devices 62a and 62b mounted on a base 61 including the signal processing unit 8 and is provided on the side opposite to the side of the polarized light filter 4 through the spacer 5. The image pickup regions of the two solid-state image pickup devices 62a and 62b where a subject image is to be actually formed are provided on the same plane parallel to the XY-plane about the light axes 7a and 7b, respectively. The solid-state image pickup devices 62a and 62b do not have a color filter inside them when performing black-and-white sensing. On the other hand, the solid-state image pickup devices 62a and 62b may have a color filter arranged before them when performing color sensing.

Thus, the image pickup apparatus 1 has a dual optical system that picks up the vertically polarized light image and the horizontally polarized light image of the liquid droplets 200 attached to the screen 100, and is configured such that space between the lens array 2 and the solid-state image pickup unit 6 is sealed to prevent foreign matter such as dust from entering the image pickup regions of the solid-state image pickup devices 62a and 62b.

Figure 4:
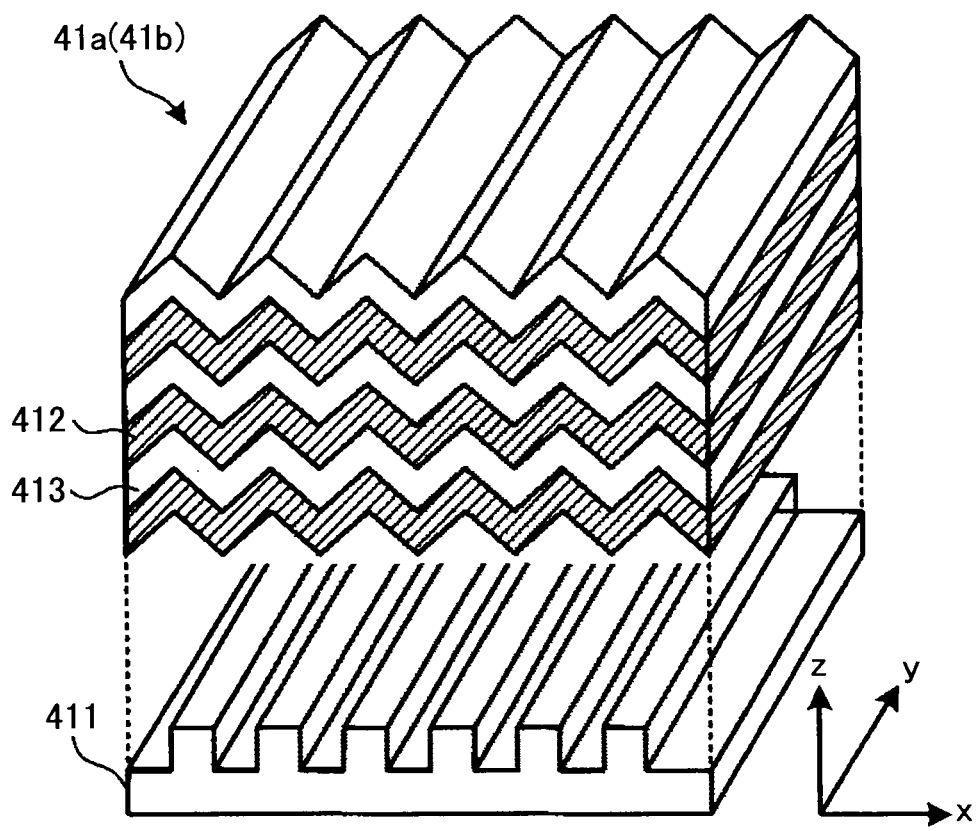
FIG. 4 is a perspective view showing the configuration of polarizer regions of a polarized light filter.

The polarizer regions 41a and 41b of the polarized light filter 4 of the image pickup apparatus 1 are polarizers made of, for example, photonic crystal. As shown in FIG. 4, transparent medium layers 412 with a high refractive index and transparent medium layers 413 with a low refractive index are alternately laminated together on a transparent substrate 411 having periodic groove rows while maintaining the shapes of their interfaces. Each of the medium layers 412 with a high refractive index and the medium layers 413 with a low refractive index has periodicity in an X-direction orthogonal to the groove rows of the transparent substrate 411. However, the medium layers 412 and the medium layers 413 may be uniform in a Y-direction parallel to the groove rows or may have a periodic or non-periodic structure greater than that in the X-direction. Such a fine periodic structure (photonic crystal) can be manufactured with good reproducibility and high uniformity according to a method called a self cloning technique.

Figure 5A:
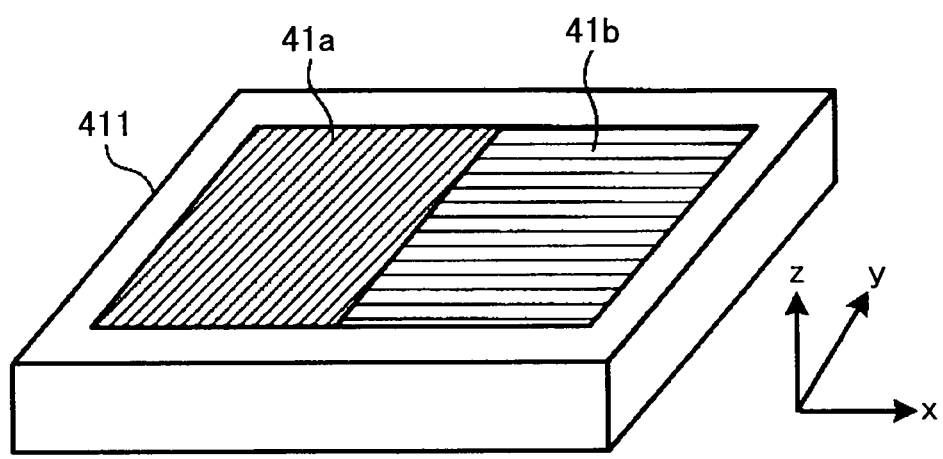
FIGS. 5A and 5B are perspective views showing the configuration of the polarized light filter.
Figure 5B:
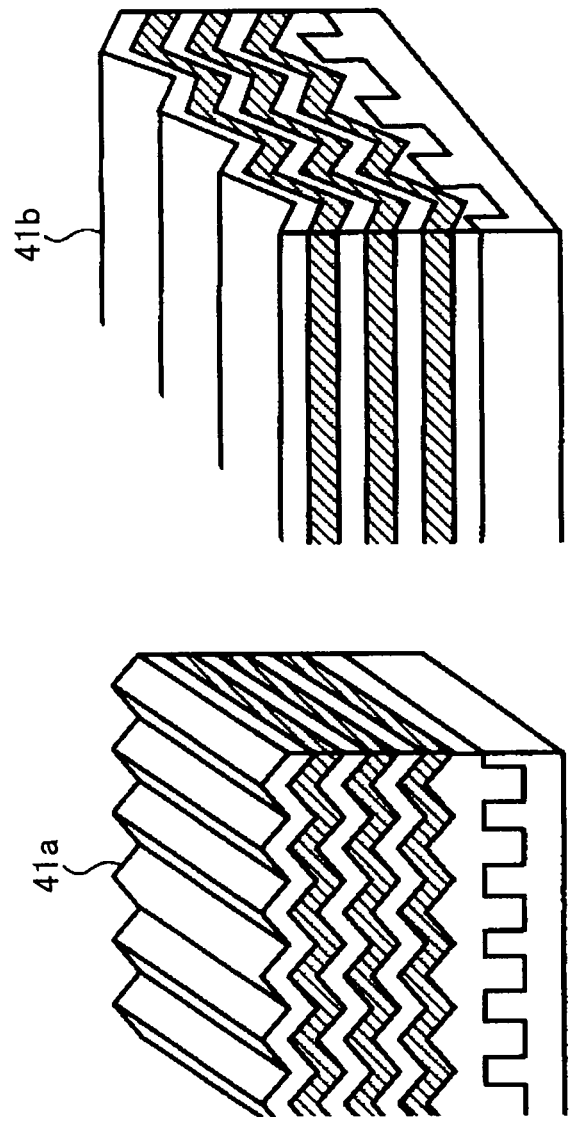

As shown in a perspective view in FIG. 5A, the polarizer regions 41a and 41b made of the photonic crystal have a multilayer structure (for example, an alternate multilayer film of $Ta_2O_5$ and $SiO_2$) in which two or more types of transparent materials are alternately laminated together in a Z-axis direction on the substrate 411 parallel to the XY-plane in an orthogonal coordinate system having a Z-axis parallel to the light axes 7a and 7b and an XY-plane orthogonal to the Z-axis. Each film of the polarizer regions 41a and 41b has irregularities, which are repeatedly formed in one direction of the XY-plane in a periodic manner. As shown in FIG. 5B, the direction of the grooves in the polarizer region 41a is parallel to the Y-axis direction, and the direction of the grooves in the polarizer region 41b is parallel to the X-axis direction. The direction of the grooves in the polarizer region 41a is different by 90° from that of the grooves in the polarizer region 41b. That is, the polarizer regions 41a and 41b are configured to allow polarized light components having different polarized light directions out of input light incident on the XY-plane to pass through while allowing non-polarized light components of the same amount to pass through. Note that the two types of irregularities are formed in the polarized light filter 4, but the irregularities may be formed in plural directions. Since the polarizer regions 41a and 41b made of the photonic crystal are resistant to ultraviolet degradation, they can be reliably used for a long period of time.

The image pickup apparatus 1 is arranged such that the direction of the grooves of any of the polarizer regions 41a and 41b, e.g., the polarizer region 41b, of the polarized light filter 4 is parallel to the screen 100. Thus, the polarizer regions 41a and 41b obtain the vertically polarized light image and the horizontally polarized light image of reflection light of the liquid droplets 200 attached to the screen 100.

As shown in FIG. 2, the signal processing unit 8 provided in the substrate 61 of the solid-state image pickup unit 6 of the image pickup apparatus 1 has signal preprocessing units 81a and 81b, image memories 82a and 82b, an image position correction unit 83, a calculation processing unit 84, a liquid droplet determination unit 85, and an output unit 86. The signal preprocessing units 81a and 81b perform shading correction or the like for correcting the sensitivity unevenness or the like of image signals output from the solid-state image pickup devices 62a and 62b of the solid-state image pickup unit 6 and store a vertically polarized light image and a horizontally polarized light image in the image memories 82a and 82b. The image position correction unit 83 corrects a parallax positional shift between the vertically polarized light image and the horizontally polarized light image stored in the image memories 82a and 82b. The calculation processing unit 84 calculates a polarized light ratio of the vertically polarized light image to the horizontally polarized light image whose positional shifts are corrected by the image position correction unit 83. The liquid droplet determination unit 85 determines whether the liquid droplets 200 are attached to the screen 100 based on the polarized light ratio calculated by the calculation processing unit 84. The output unit 86 outputs a result determined by the liquid droplet determination unit 85 to a display apparatus, a wiper control apparatus, or the like (not shown).

Figure 6:
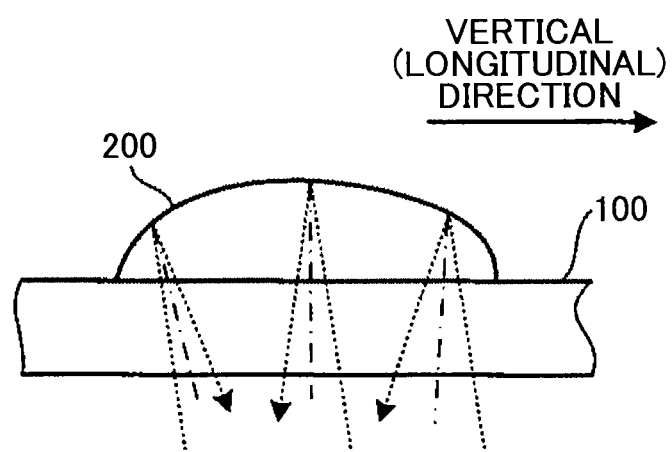
FIG. 6 is a schematic view showing a liquid droplet attached to a screen.
Figure 7B:
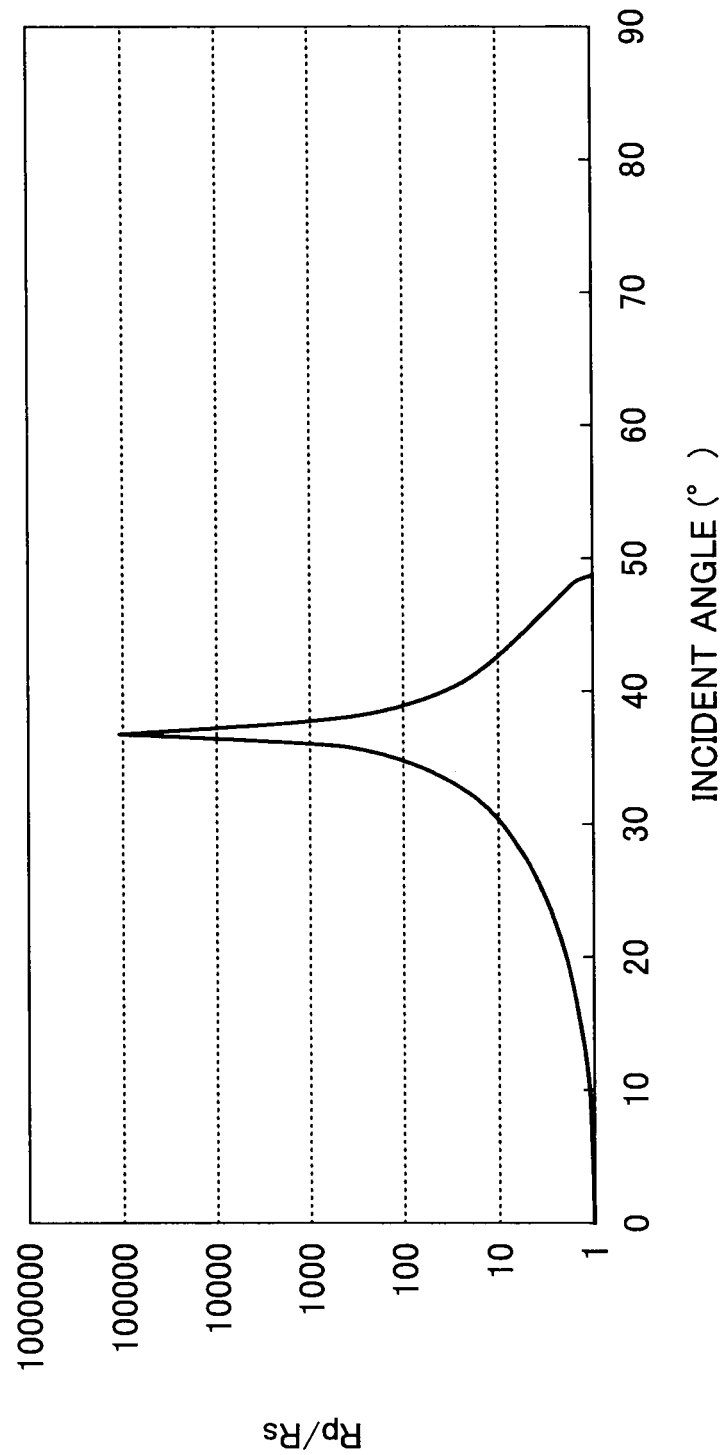
Figure 8:
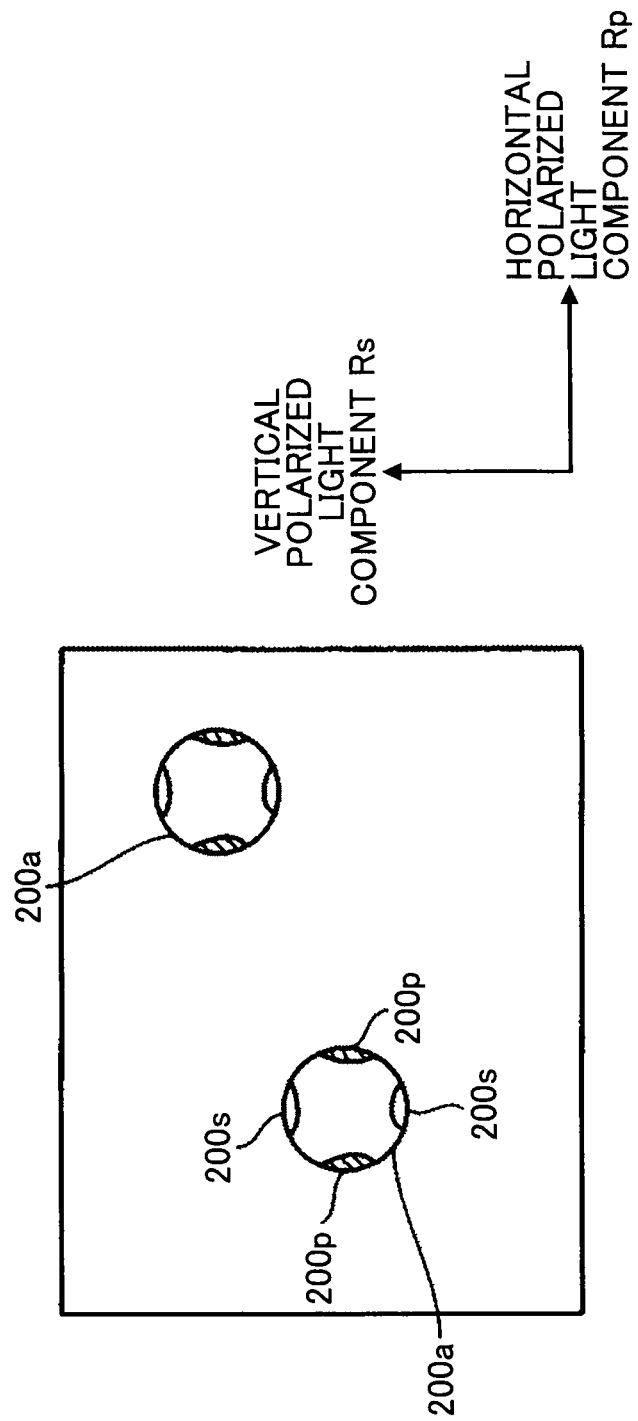
FIG. 8 is a perspective view showing a liquid droplet image having the horizontally polarized light component and the vertically polarized light component.

Prior to describing operations when the liquid droplet recognition apparatus detects the liquid droplets 200 attached to the screen 100, a description is first made of the operating principle of detecting the liquid droplets 200 according to polarized light characteristics as a feature of the embodiment of the present invention. As shown in FIG. 6, when parallel light flux is applied to the screen 100 having the liquid droplet 200 attached on its front surface from the side of the screen 100, an incident angle of the light, which is incident on an interface between the liquid droplet 200 and air after passing through the screen 100, is different depending on positions of incidence on the convex spherical surface of the liquid droplet 200. Therefore, a reflection amount of the light is also different depending on the positions. For example, as shown in FIG. 7A, the light, which is applied from the inside of the screen 100 to the screen 100 having a waterdrop with a refractive index of 1.33 attached at its front surface and is incident on and reflected by an interface between the waterdrop and air with a refractive index of 1, has greatly different reflectance depending on incident angles. In addition, the reflectance of a horizontally polarized light component Rp and a vertically polarized light component Rs is different depending on the incident angles. Thus, a reflectance characteristic at the interface between the convex spherical surface of the liquid droplet 200 and air is different between the horizontally polarized light component Rp and the vertically polarized light component Rs. Therefore, for example, when the incident angle of the light applied to a peripheral part in the longitudinal (vertical) direction of the liquid droplet 200 is about 40°, the horizontally polarized light component Rp becomes greater than the vertically polarized light component Rs, and a polarized light ratio Rp/Rs of the horizontally polarized light component to the vertically polarized light component shows a characteristic having a peak as shown in FIG. 7B. Meanwhile, as for the lateral (horizontal) direction of the liquid droplet 200, the directions of the polarized light components as the reflectance characteristics are inverted. Therefore, the vertically polarized light component Rs becomes greater than the horizontally polarized light component Rp, and the polarized light ratio Rs/Rp shows a characteristic having a peak as in the case of FIG. 7B (a vertical axis in FIG. 7B is set as Rs/Rp). Here, based on a pickup image (pickup device), the longitudinal direction of the pickup image (pickup device) is assumed to be a vertical direction and the lateral direction thereof is assumed to be a horizontal direction. According to this principle, images of the horizontally polarized light component Rp and the vertically polarized light component Rs of light reflected by the interface between air and the liquid droplet 200 attached to the screen 100 are obtained, and the polarized light ratio Rp/Rs of the horizontally polarized light component Rp to the vertically polarized light component Rs is calculated. Therefore, since the polarized light ratio Rp/Rs increases in the vicinity of the boundary of the image of the liquid droplet 200, the characteristics of the liquid droplet 200 can be extracted. In addition, as shown in a schematic diagram in FIG. 8, the brightness of boundary neighboring regions 200p of the horizontally polarized light components in the lateral direction is inverted by the brightness of boundary neighboring regions 200s of the vertically polarized light components in the longitudinal direction. This phenomenon does not occur even if dust or the like forming no convex spherical surface at an interface with air is attached to the screen 100 and is peculiar to a case where the liquid droplets 200 are attached to the screen 100. With the confirmation of this phenomenon, the liquid droplet recognition apparatus can determine the presence or absence of the liquid droplets 200 on the screen 100.

Next, a description is made of the operations when the liquid droplet recognition apparatus detects the liquid droplets 200 attached to the screen 100. The image pickup apparatus 1 is arranged such that the direction of the grooves of any of the polarizer regions 41a and 41b, e.g., the polarizer region 41b, of the polarized light filter 4 of the image pickup apparatus 1 is parallel to the screen 100. Then, light is applied from the light source 10 to an image pickup region of the screen 100 to pick up an image. The light flux applied to the image pickup lens 21a of the lens array 2 is incident on the polarizer region 41a of the polarized light filter 4 through the light-shielding spacer 3. The polarizer region 41a allows only the light of the vertically polarized light component Rs to pass through the solid-state image pickup device 62a of the solid-state image pickup unit 6. Furthermore, the light flux applied to the image pickup lens 21b of the lens array 2 is incident on the polarizer region 41b of the polarized light filter 4 through the light-shielding spacer 3. The polarizer region 41b allows only the light of the horizontally polarized light component Rp to pass through the solid-state image pickup device 62b of the solid-state image pickup unit 6. Image signals picked up by and output from the solid-image image pickup devices 62a and 62b are processed by the signal preprocessing units 81a and 81b of the signal processing unit 8, so that a vertically polarized light image and a horizontally polarized light image are stored in the image memories 82a and 82b, respectively. The vertically polarized light image and the horizontally polarized light image stored in the image memories 82a and 82b are output to the calculation processing unit 84 with their parallax positional shifts corrected by the image position correction unit 83. The calculation processing unit 84 first calculates the polarized light ratio Rp/Rs of the horizontally polarized light component Rp to the vertically polarized light component Rs of the input images. Then, the calculation processing unit 84 calculates the polarized light ratio Rp/Rs in the image boundary neighboring region of the liquid droplets 200 and outputs the same to the liquid droplet determination unit 85. The liquid droplet determination unit 85 compares the input polarized light ratio Rp/Rs with a specified reference value and determines the presence or absence of the liquid droplets 200 on the screen 100 based on whether the input polarized light ratio Rp/Rs exceeds the reference value. When it is determined that the liquid droplets 200 are attached to the screen 100, the liquid droplet determination unit 85 outputs a distribution amount of the liquid droplets 200 in the image output from the image position correction unit 83 to the output unit 86. When the input determination result shows that the liquid droplets 200 are attached to the screen 100, the output unit 86 outputs both the presence of the liquid droplets 200 on the screen 100 and the distribution amount of the liquid droplets 200 to a display device (not shown) so as to be displayed.

Thus, the liquid droplet recognition apparatus can reliably detect the presence or absence of the liquid droplets 200 on the screen 100 and the distribution amount of the liquid droplets 200 with a simple configuration. Furthermore, since the image position correction unit 83 corrects the parallax positional shifts of the vertically polarized light image and the horizontally polarized light image emitted from the two lenses 21a and 21b of the lens array 2 of the image pickup apparatus 1, the liquid droplet recognition apparatus can obtain a high-quality image. Furthermore, since the calculation processing unit 84 calculates the polarized light ratio Rp/Rs in the image boundary neighboring region of the liquid droplets 200 and the liquid droplet determination unit 85 compares the calculated polarized light ratio Rp/Rs with a specified reference value, the liquid droplet recognition apparatus can reliably detect the presence or absence of the liquid droplets 200 on the screen 100.

Figure 9:
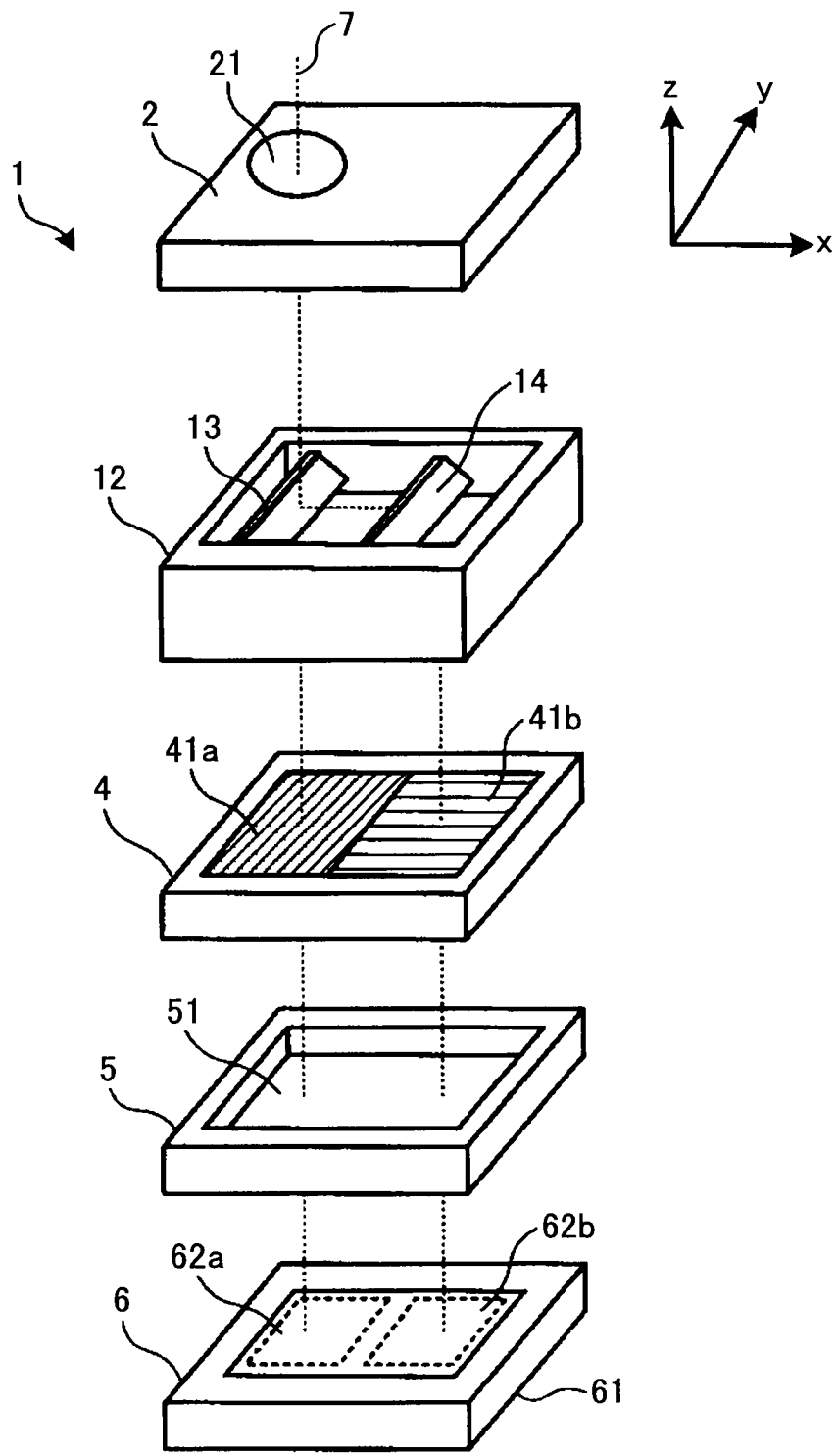
FIG. 9 is an exploded perspective view showing the configuration of a second image pickup apparatus.
Figure 10:
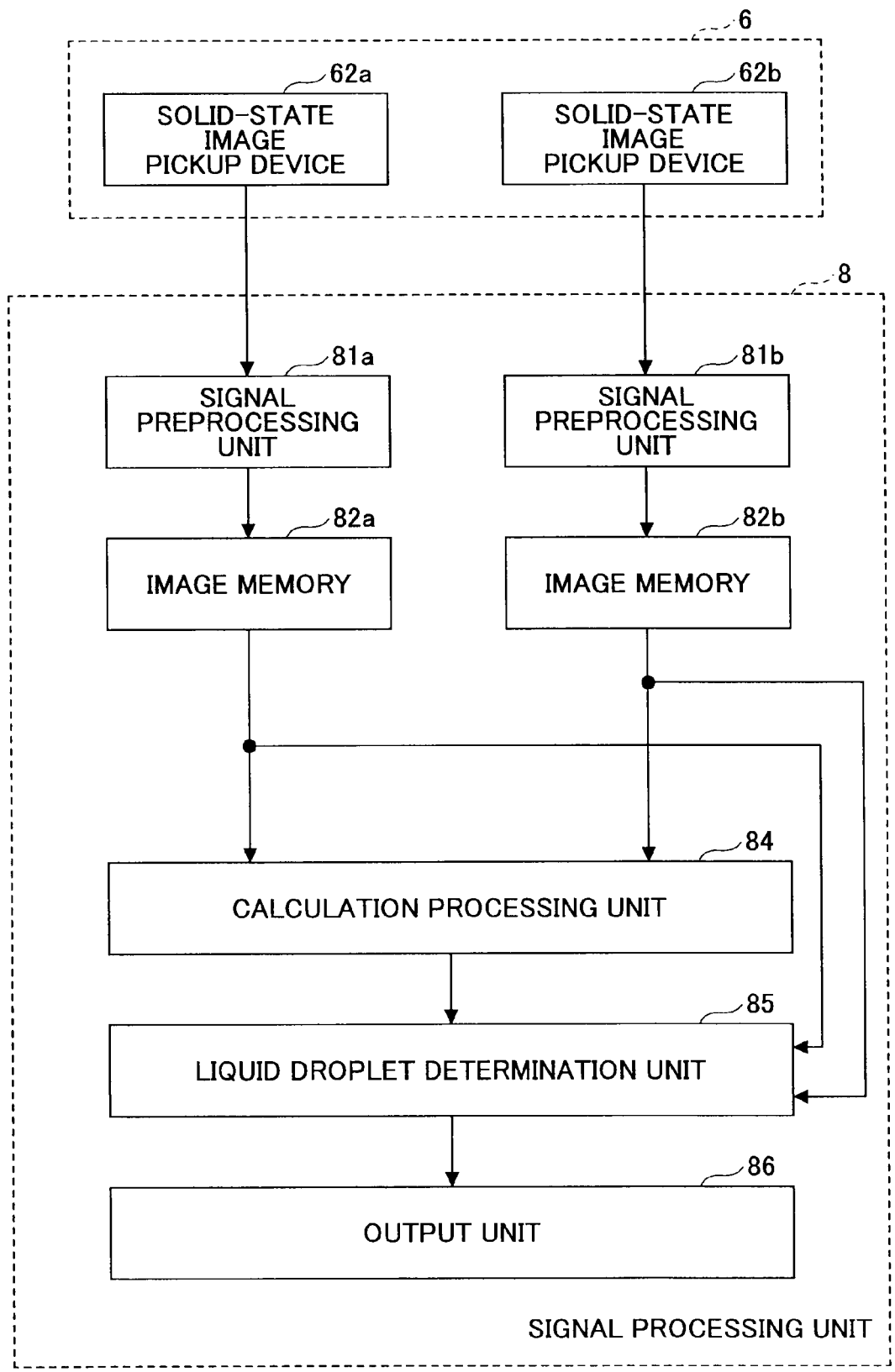
FIG. 10 is a block diagram showing the configuration of a second signal processing unit.

In the above description, the image pickup apparatus 1 is configured to have the two image pickup lenses 21a and 21b in the lens array 2. However, as shown in FIG. 9, the image pickup apparatus 1 may be configured to have a single image pickup lens 21 in the lens array 2 and a beam splitter 12 provided with a half mirror or prism 13 and a mirror 14 at the subsequent stage of the image pickup lens 21 so that the light incident on the image pickup lens 21 is separated and transmitted into two systems. If the liquid droplet 200 attached to the screen 100 is thus picked up by the single image pickup lens 21 provided in the lens array 2, the image pickup apparatus 1 has a smaller detection region requirement and eliminates the correction of parallax positional shifts. Therefore, as shown in a block diagram in FIG. 10, the image position correction unit 83 is not required in the signal processing unit 8, which in turn can simplify the configuration of the signal processing unit 8.

Figure 11:
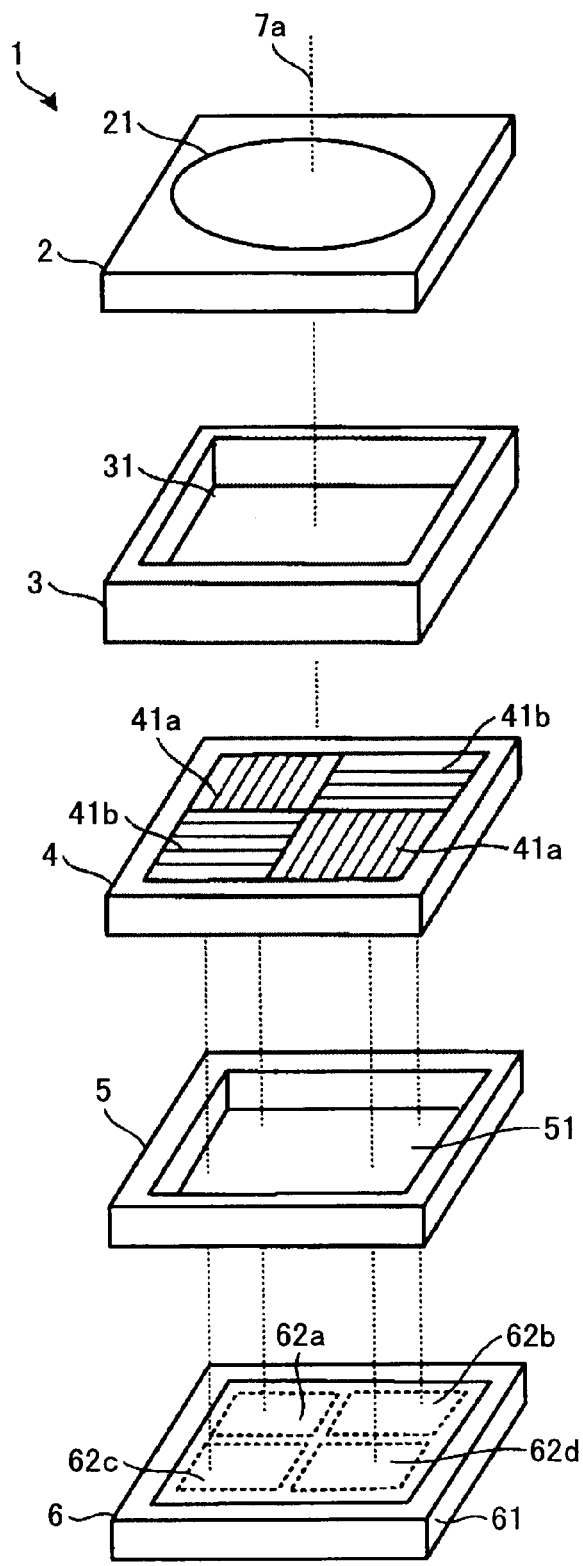
FIG. 11 is an exploded perspective view showing the configuration of a third image pickup apparatus.

Furthermore, as shown in FIG. 11, the image pickup apparatus 1 may be configured to have a single image pickup lens 21 having a large diameter in the lens array 2, plural polarizer regions 41a that allow only a vertically polarized light component to pass through and polarizer regions 41b that allow only a horizontally polarized light component to pass through in the polarized light filter 4, and plural solid-state image pickup devices 62a through 62d corresponding to the plural polarizer regions 41a and 41b of the polarized light filter 4 in the solid-state image pickup unit 6. In this case, the image pickup apparatus 1 can obtain a vertically polarized light image and a horizontally polarized light image from the light flux of the same axis emitted from the single image pickup lens 21. Therefore, since the image pickup device does not require the beam splitter 12, it can be downsized.

In the above description, the liquid droplet recognition apparatus determines that the liquid droplets 200 are attached to the transparent screen 100. The liquid droplet recognition apparatus can be applied to transparent members such as windshields, rear windows, and side windows of vehicles. In particular, the liquid droplet recognition apparatus is best suited to windshields that are significantly influenced by liquid droplets.

Furthermore, the liquid droplet recognition apparatus may detect the liquid droplets 200 attached to the front surface of the transparent screen 100 based on a polarized light image ratio obtained by picking up a vertically polarized light image and a horizontally polarized light image from the side of the front surface of the transparent screen 100 to which the liquid droplets 200 are attached. However, in order to protect the image pickup apparatus 1 from dust or the liquid droplets 200 and be able to easily install the liquid droplet recognition apparatus in a vehicle without disfiguring the appearance of the vehicle, it is most appropriate that the liquid droplet recognition apparatus picks up images to detect the liquid droplets 200 from the side of the rear surface of the transparent screen 100.

Figure 12:
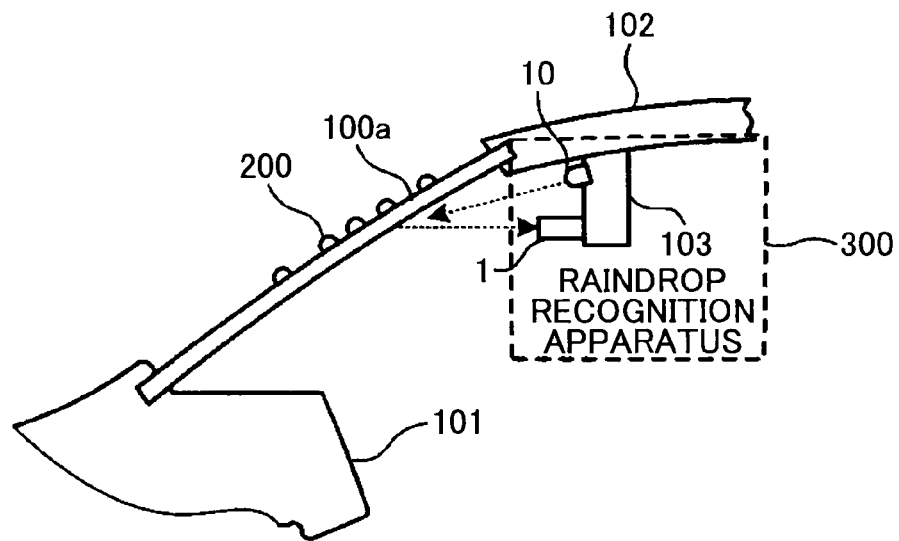
FIG. 12 is a diagram showing the arrangement of a raindrop recognition apparatus mounted on a vehicle.

Referring next to FIG. 12 showing the driver's seat area of a vehicle, a description is made of a raindrop recognition apparatus 300 that detects raindrops attached to the windshield of the vehicle by using the liquid droplet recognition apparatus described above. In FIG. 12, reference numeral 100a denotes the windshield of the vehicle, reference numeral 101 denotes a dashboard, reference numeral 102 denotes the roof of the vehicle, and reference numeral 103 denotes a rearview mirror. The image pickup apparatus 1 and the light source 10 are mounted on the rear surface of the rearview mirror 103. The light source 10 irradiates a region of the windshield 100a with illumination light to be picked up by the image pickup apparatus 1. The illumination light irradiated from the light source 10 is near-infrared illumination light that is not visible to human eyes and does not affect the human eyes. The image pickup apparatus 1 is arranged such that the direction of the grooves of any of the polarizer regions 41a and 41b, e.g., the polarizer region 41b, is parallel to the windshield 100a. The image pickup apparatus 1 is aligned to a prescribed image pickup region of the windshield 100a to obtain a vertically polarized light image and a horizontally polarized light image and outputs the obtained vertically polarized light image and the horizontally polarized light image to the signal processing unit 8. The signal processing unit 8 processes the input vertically polarized light image and the horizontally polarized light image to determine the presence or absence of the raindrops 200 on the windshield 100a. When it is determined that the raindrops 200a are attached to the windshield 100a, the signal processing unit 8 calculates a distribution amount of the raindrops 200 and outputs both the presence of the raindrops 200 on the windshield 100a and the distribution amount of the raindrops 200 to a display device (not shown) so as to be displayed.

Figure 13:
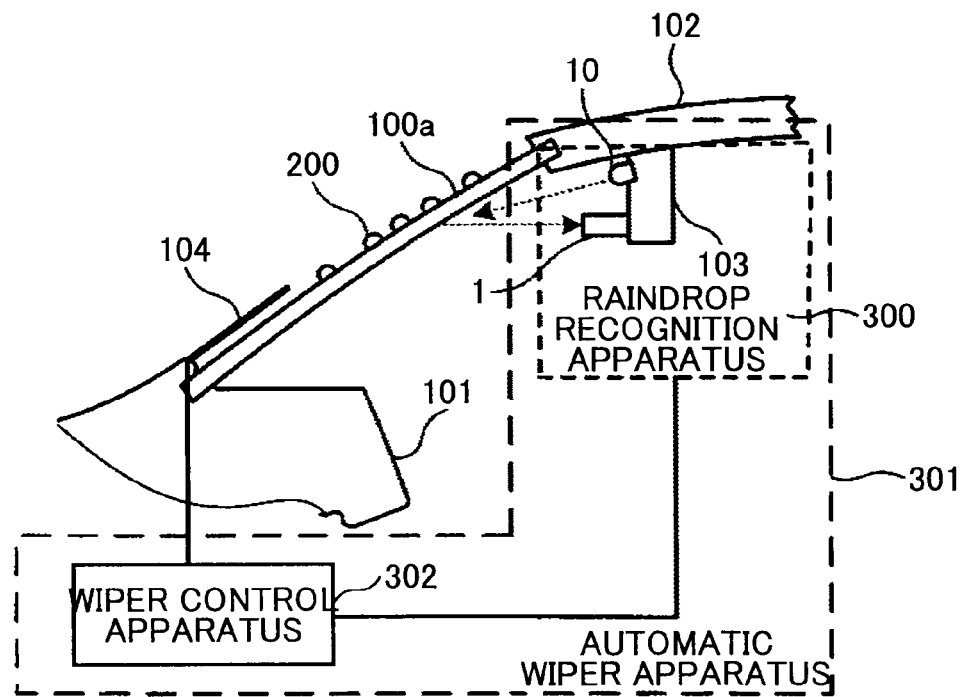
FIG. 13 is a configuration diagram of an automatic wiper apparatus having the raindrop recognition apparatus.
Figure 14:
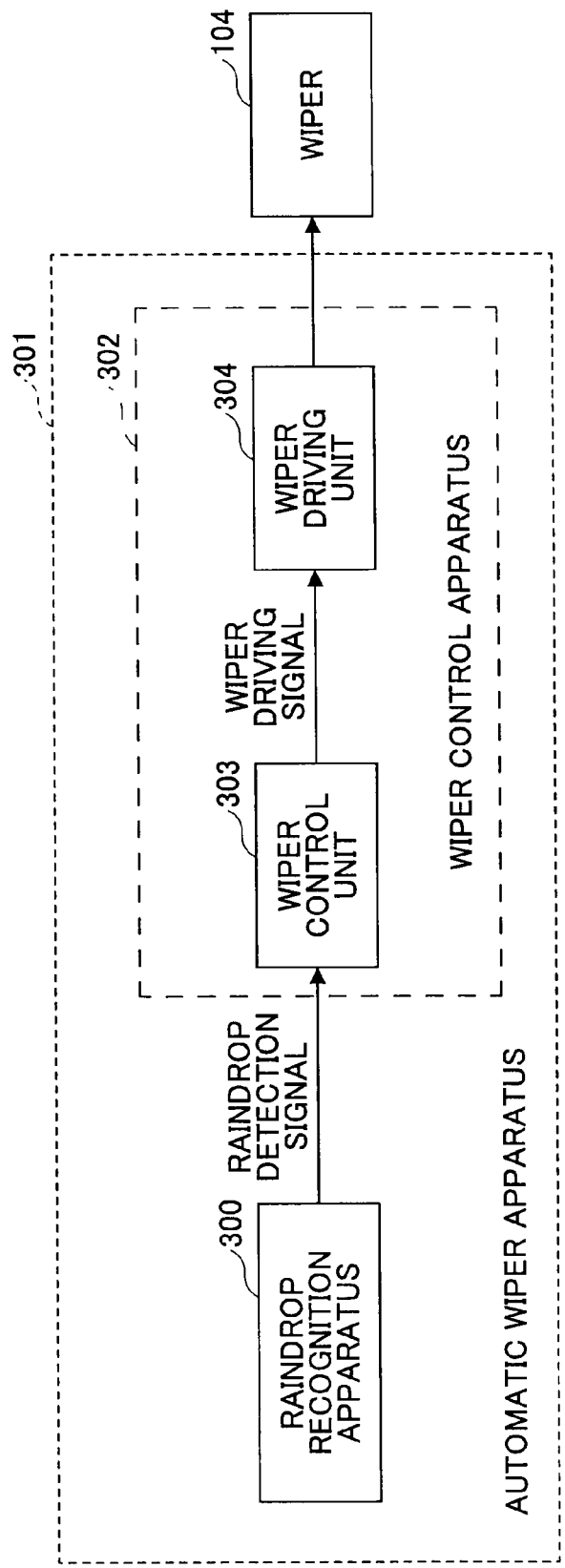
FIG. 14 is a block diagram showing the configuration of the automatic wiper apparatus.

Referring then to a configuration diagram in FIG. 13 and a block diagram in FIG. 14, a description is made of an automatic wiper apparatus 301 that detects the raindrops 200 attached to the windshield 100a of a vehicle by using the raindrop recognition apparatus 300 and controls a wiper 104 that wipes off the raindrops 200. The basic configuration of the automatic wiper apparatus 301 is the same as that shown in FIG. 12. As shown in FIG. 13, the automatic wiper apparatus 301 has the raindrop recognition apparatus 300 and a wiper control apparatus 302 that controls the wiper 104 for wiping off the raindrops 200 attached to the windshield 100a. As shown in FIG. 14, the wiper control apparatus 302 is composed of a wiper control unit 303 such as a microcomputer that outputs a driving signal to the wiper 104 and a wiper driving unit 304 such as a motor that drives the wiper 104.

In the automatic wiper apparatus 301, when a distribution amount of the recognized raindrops 200 exceeds a certain reference value, the raindrop recognition apparatus 300 outputs a raindrop detection signal to the wiper control apparatus 302. The wiper control unit 303 of the wiper control apparatus 302 outputs a wiper driving signal to the wiper driving unit 304 in accordance with the raindrop detection signal to drive the wiper 104. The reference value of the distribution amount of the raindrops 200 for driving the wiper 104 is set according to the type, strength, and amount of rain, and the raindrop detection signal is set according to a specific reference value of the distribution amount of the raindrops 200. That is, the automatic wiper apparatus 301 realizes on and off operations, switching between an intermittent operation and a successive operation, and controlling a time interval in the intermittent operation or an operating speed in the successive operation.

As described above, the raindrop recognition apparatus 300 determines the presence or absence of the raindrops 200 on the windshield 100a based on the polarized light ratio Rp/Rs in the image boundary neighboring region of the horizontally polarized light component Rp, to the vertically polarized light component Rs of the image picked up by the image pickup apparatus 1 according to the phenomenon peculiar to the raindrops 200 having a convex spherical surface at an interface with air. Therefore, even if dust or the like is attached to the windshield 100a, the raindrop recognition apparatus 300 can reliably recognize only the raindrops 200 attached to the windshield 100a without falsely recognizing dust or the like. Furthermore, the raindrop recognition apparatus 300 determines the presence or absence of the raindrops 200 based on the polarized light ratio Rp/Rs in the image boundary neighboring region of the horizontally polarized light component to the vertically polarized light component of the image picked up by the image pickup apparatus 1, so that the raindrop recognition device 300 is free from the influences of surrounding brightness variations.

(Second Embodiment)

Figure 15:
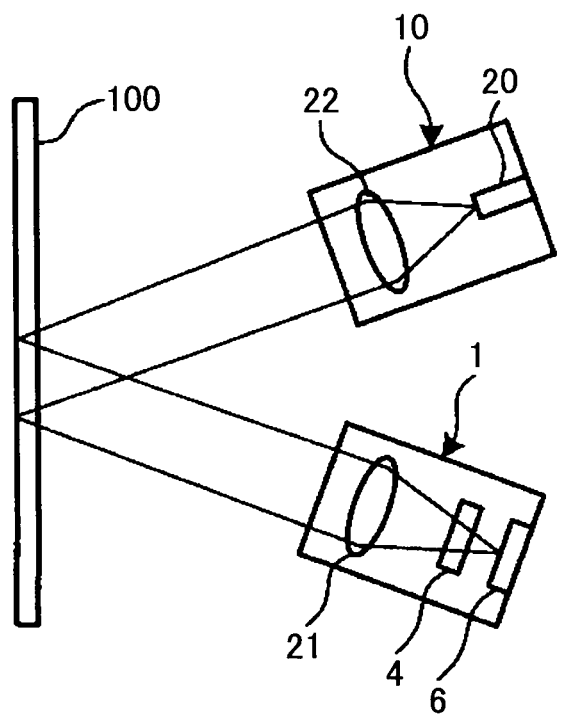
FIG. 15 is a configuration diagram of an optical system of a raindrop detection apparatus according to a second embodiment of the present invention.
Figure 16:
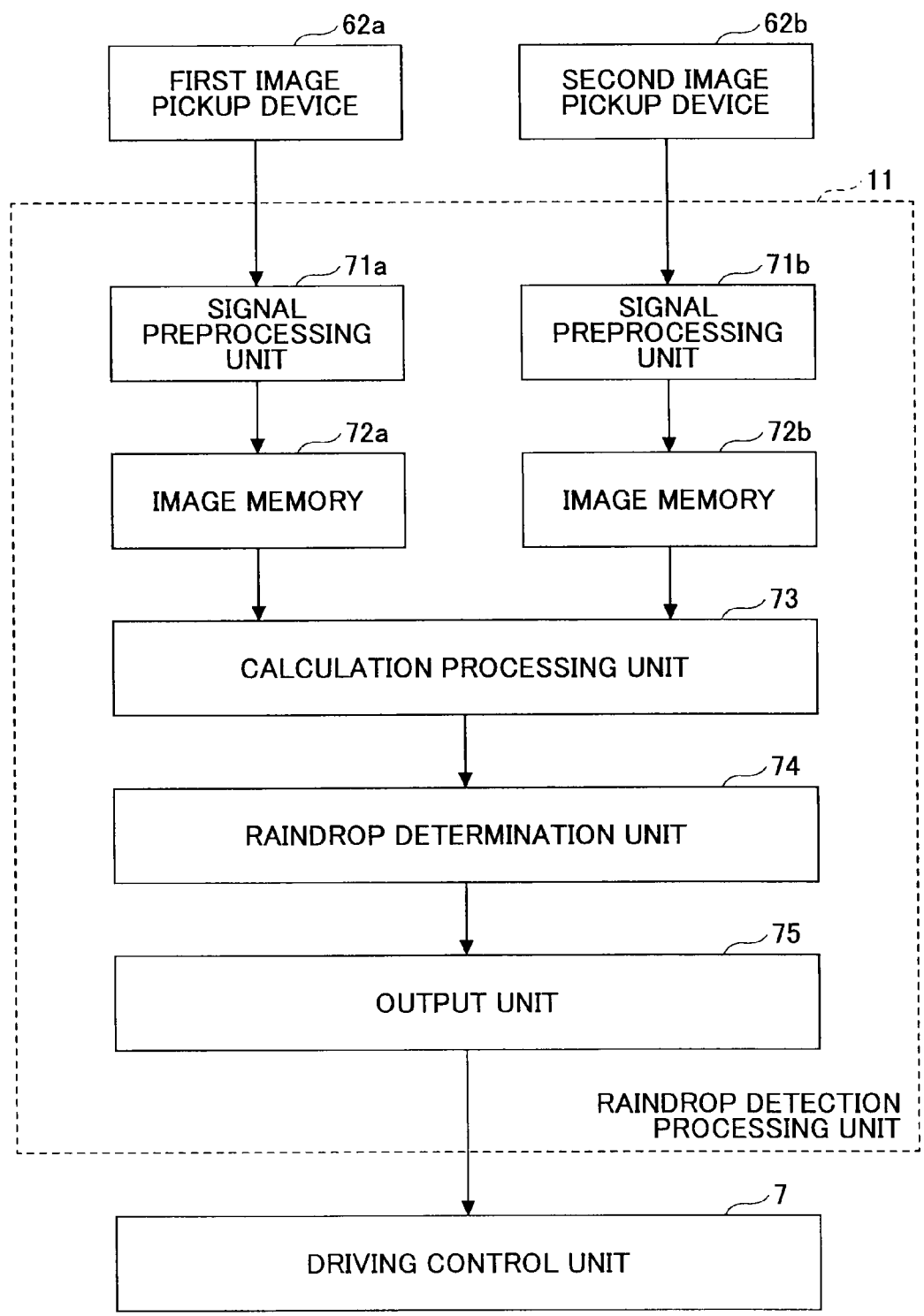
FIG. 16 is a block diagram showing the configuration of a raindrop detection processing unit of the raindrop detection apparatus.

FIGS. 15 and 16 show the configuration of a raindrop detection apparatus according to a second embodiment of the present invention, wherein FIG. 15 is a configuration diagram of an optical system and FIG. 16 is a block diagram showing the configuration of a raindrop detection processing unit. As shown in FIG. 15, the optical system of the raindrop detection apparatus is composed of an image pickup apparatus 1 and a light source 10. With this configuration, the raindrop detection apparatus picks up an image of raindrops attached to the front surface of a windshield 100 of a vehicle. The light source 10 has a light-emitting device 20 such as a LED and a lens 22. The light source 10 converts light emitted from the light-emitting device 20 into parallel light flux through the lens 22 and applies the parallel light flux to the windshield 100. The light source 10 is arranged such that the parallel light flux is incident on the windshield 100 at Brewster's angle θB (θB=57°). The image pickup apparatus 1 picks up an image of the light emitted from the light source 10 and reflected by the windshield 100.

Figure 17:
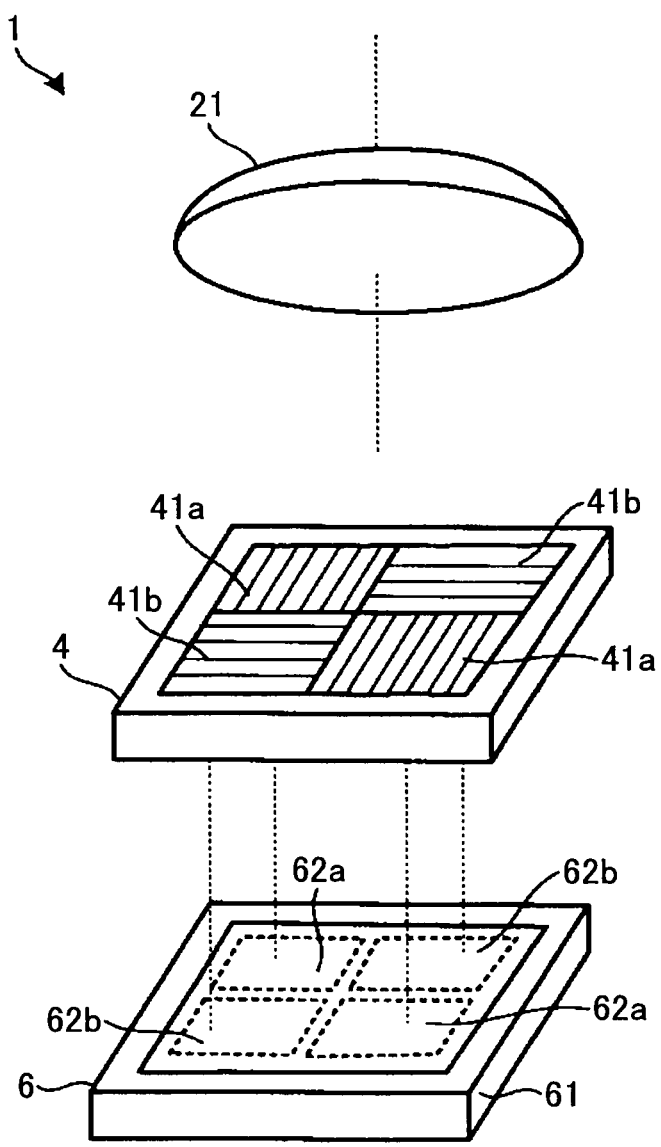
FIG. 17 is an exploded perspective view showing the configuration of an image pickup apparatus of the raindrop detection apparatus.

As shown in an exploded perspective view in FIG. 17, the image pickup apparatus 1 is composed of an image pickup lens 21, a polarized light filter 4, and a solid-state image pickup unit 6. The polarized light filter 4 has plural polarizer regions 41a that allow only the light of an S-polarized light component to pass through and polarizer regions 41b that allow only the light of a P-polarized light component to pass through. The solid-state image pickup unit 6 has plural first image pickup devices 62a and second image pickup devices 62b mounted on a substrate 61 having a raindrop detection processing unit 11 so as to correspond to the plural polarizer regions 41a and 41b of the polarized light filter 4, respectively. The plural first image pickup devices 62a and second image pickup devices 62b do not have a color filter inside them when performing black-and-white sensing. On the other hand, the plural first image pickup devices 62a and second image pickup devices 62b may have a color filter arranged before them when performing color sensing.

The polarizer regions 41a and 41b of the polarized light filter 4 of the image pickup apparatus 1 are polarizers made of, for example, photonic crystal. As shown in a perspective view in FIG. 18A, transparent medium layers 412 with a high refractive index and transparent medium layers 413 with a low refractive index are alternately laminated together on a transparent substrate 411 having periodic groove rows while maintaining the shapes of their interfaces. Each of the medium layers 412 with a high refractive index and the medium layers 413 with a low refractive index has periodicity in an X-direction orthogonal to the groove rows of the transparent substrate 411. However, the medium layers 412 and the medium layers 413 may be uniform in a Y-direction parallel to the groove rows or may have a periodic or non-periodic structure greater than that in the X-direction. Such a fine periodic structure (photonic crystal) can be manufactured with good reproducibility and high uniformity according to a method called a self cloning technique.

Figure 18A:
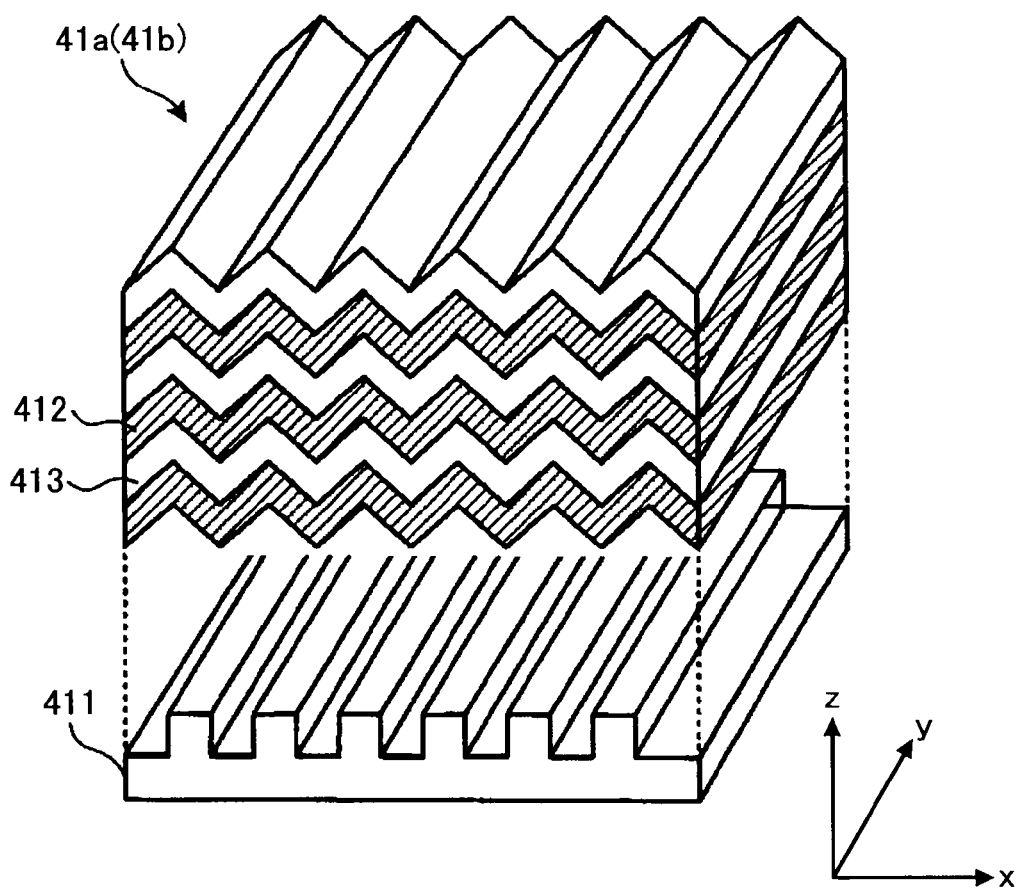
FIGS. 18A and 18B are perspective views showing the configuration of a polarized light filter.
Figure 18B:
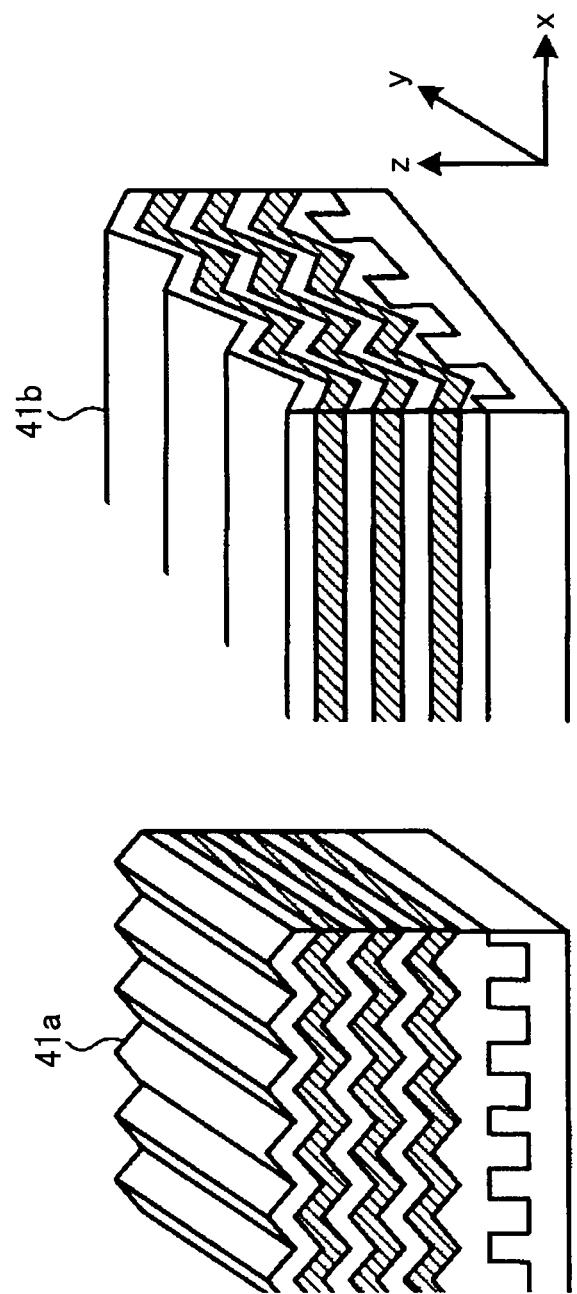

As shown in perspective view in FIG. 18A, the polarizer regions 41a and 41b made of the photonic crystal have a multilayer structure (for example, an alternate multilayer film of $Ta_2O_5$ and $SiO_2$) in which two or more types of transparent materials are alternately laminated together in a Z-axis direction on the substrate 411 parallel to the XY-plane in an orthogonal coordinate system having a Z-axis parallel to a light axis and an XY-plane orthogonal to the Z-axis. Each film of the polarizer regions 41a and 41b has irregularities, which are repeatedly formed in one direction of the XY-plane in a periodic manner. The direction of the grooves in the polarizer region 41a is parallel to the Y-axis direction, and the direction of the grooves in the polarizer region 41b is parallel to the X-axis direction. The direction of the grooves in the polarizer region 41a is different by 90° from that of the grooves in the polarizer region 41b. That is, the polarizer regions 41a and 41b are configured to allow polarized light components having different polarized light directions out of input light applied to the XY-plane to pass through. Since the polarizer regions 41a and 41b made of the photonic crystal are resistant to ultraviolet degradation, they can be reliably used for a long period of time.

The image pickup apparatus 1 is arranged such that the direction of the grooves of any of the polarizer regions 41a and 41b, e.g., the polarizer region 41b, of the polarized light filter 4 is parallel to the windshield 100. Thus, the polarizer regions 41a and 41b obtain a vertically polarized light image and a horizontally polarized light image of reflection light of the raindrops 200 attached to the windshield 100.

As shown in FIG. 16, the raindrop detection processing unit 11 provided in the substrate 61 of the solid-state image pickup unit 6 of the image pickup apparatus 1 has signal preprocessing units 71a and 71b, image memories 72a and 72b, a calculation processing unit 73, a raindrop determination unit 74, and an output unit 75. The signal preprocessing units 71a and 71b perform shading correction or the like for correcting the sensitivity unevenness or the like of image signals output from the first image pickup devices 62a and the second image pickup devices 62b of the solid-state image pickup unit 6 and store an S-polarized light image and a P-polarized light image in the image memories 72a and 72b. The calculation processing unit 73 calculates a reflectance difference (strength difference) between the S-polarized light image and the P-polarized light image stored in the image memories 72a and 72b. The raindrop determination unit 74 determines the presence or absence of raindrops 200 on the windshield 100 and an amount of the raindrops 200 based on the reflectance difference between the S-polarized light image and the P-polarized light image calculated by the calculation processing unit 73. The output unit 75 outputs a driving signal to a driving control unit 7 that drives a wiper of a vehicle when the amount of raindrops 200 determined by the raindrop determination unit 74 reaches a specified amount.

Prior to describing operations when the raindrop recognition apparatus detects raindrops 200 attached to the windshield 100, a description is first made of its operating principle.

Figure 19:
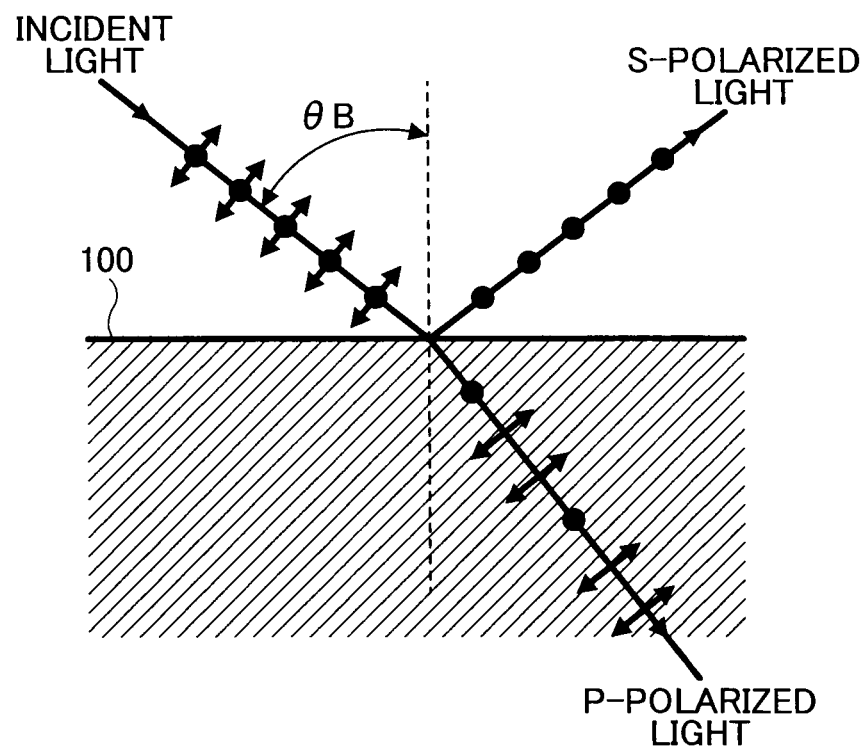
FIG. 19 is a schematic view showing incident light, reflected light, and refracted light at a windshield.
Figure 20:
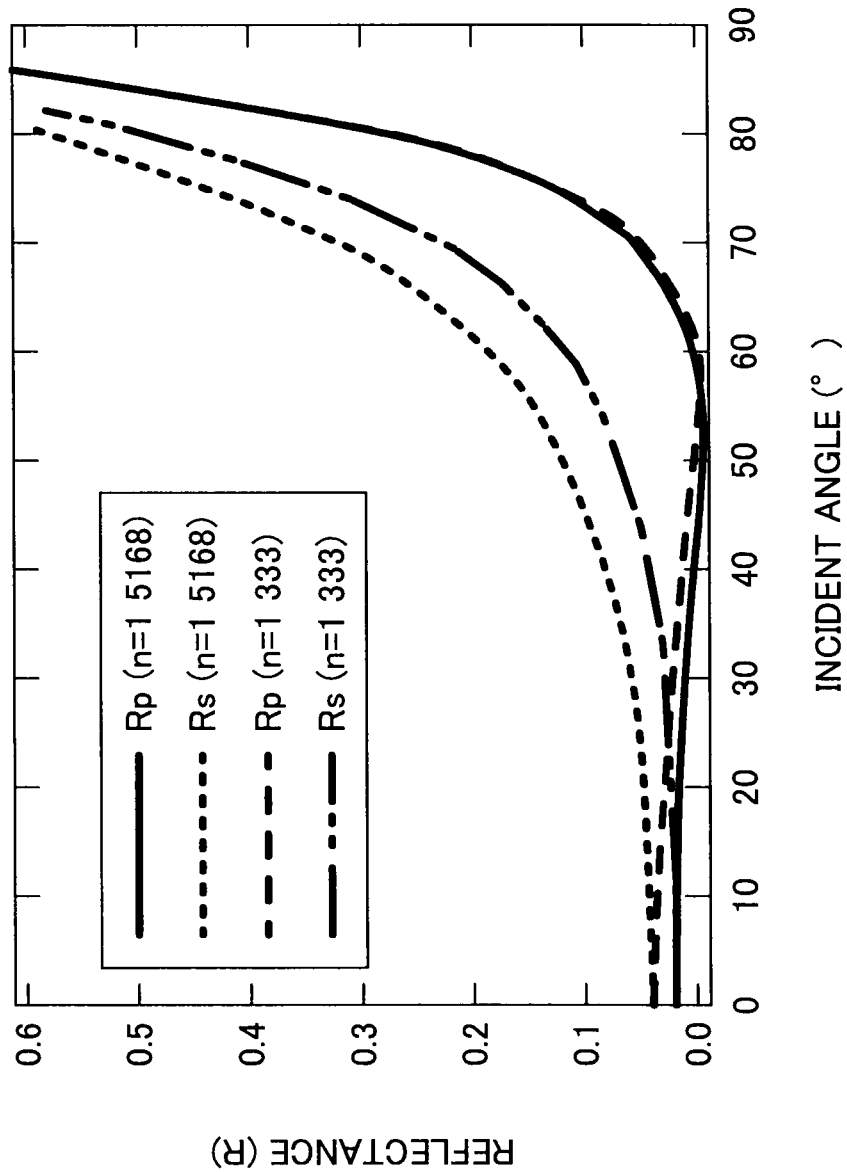
FIG. 20 is a graph showing characteristics of variations in reflectance of S-polarized light and P-polarized light reflected by the windshield.

Light emitted from the light-emitting device 20 of the light source 10 is converted into parallel light by the lens 22 and made incident on the windshield 100 (glass). Then, the light is reflected by the windshield 100 and made incident on the image pickup apparatus 1. The reflection light incident on the image pickup apparatus 1 is condensed by the image pickup lens 21 and received by the solid-state image pickup unit 11 through the polarized light filter 4. The light source 10 is arranged such that the light emitted from the light source 10 is incident on the windshield 100 at Brewster's angle θB. Therefore, only S-polarized light is reflected by the windshield 100 to which no raindrop is attached. That is, as shown in FIG. 19, when the light is incident on the windshield 100 at Brewster's angle θB (θB=57°), the P-polarized light is 0% reflected and the S-polarized light is about 20% reflected. Accordingly, only the S-polarized light is allowed to pass through the image pickup lens 21 and the polarized light filter 4 and be received by the solid-state image pickup unit 6. When it rains in such a situation, the film of water with a refractive index of n=1.33 is formed at the front surface of glass with a refractive index of n=1.5168 serving as the windshield 100. Therefore, the reflectance difference between the S-polarized light and P-polarized light of the reflection light varies as shown in FIG. 20. With the detection of the reflectance difference between the S-polarized light and the P-polarized light, the raindrop detection apparatus can detect an amount of raindrops 200.

Next, a description is made of the operations when the raindrop recognition apparatus detects liquid droplets 200 attached to the windshield 100. The image pickup apparatus 1 is arranged such that the direction of the grooves of any of the polarizer regions 41a and 41b, e.g., the polarizer region 41b, of the polarized light filter 4 of the image pickup apparatus 1 is parallel to the windshield 100. Then, light is applied from the light source 10 to an image pickup region of the windshield 100 at Brewster's angle to pick up an image of the windshield 100. When raindrops are not attached to the windshield 100 at this time, only S-polarized light is reflected by the windshield 100. The light flux applied to the image pickup lens 21 is incident on the polarizer regions 41a of the polarized light filter 4. The polarizer regions 41a allow only the light of an S-polarized light component to pass through and cause the same to be incident on the first image pickup devices 62a of the solid-state image pickup unit 6. On the other hand, the polarizer regions 41b of the polarized light filter 4 block the S-polarized light component out of the light incident on the polarizer regions 41b of the polarized light filter 4, so that the light is not incident on the image pickup devices 62b of the solid-state image pickup unit 6. Accordingly, only the first image pickup devices 62a output an image signal to the signal preprocessing unit 71a of the raindrop detection processing unit 11 so as to be processed, and only an S-polarized light image is stored in the image memory 72a. The calculation processing unit 73 calculates a reflectance difference based on the brightness of the S-polarized light image and that of the P-polarized light image stored in the image memories 72a and 72b, respectively. At this time, the S-polarized light image is stored only in the image memory 72a, and the P-polarized image is not stored in the image memory 72b. Since the S-polarized light is 100% reflected and the P-polarized light is 0% reflected, the calculation processing unit 73 outputs a calculation result to the raindrop determination unit 74 as a reflectance difference $\Delta R=(Rs-Rp)$ between the S-polarized light and the P-polarized light. When the raindrop determination unit 74 receives from the calculation processing unit 73 information indicating that the S-polarized light is 100% reflected and the P-polarized light is 0% reflected, it determines that no raindrop is attached to the windshield 100.

On the other hand, when it rains and raindrops 200 are attached to the windshield 100, S-polarized light and P-polarized light are reflected by the windshield 100, incident on the image pickup apparatus 1, and received by the first image pickup devices 62a and the second image pickup devices 62b of the solid-state image pickup unit 6 through the polarizer regions 41a and 41b. An S-polarized light image and a P-polarized light image are output from the first image pickup devices 62a and the second image pickup devices 62b to the signal preprocessing units 71a and 71b of the raindrop detection processing unit 11 so as to be processed. Then, the S-polarized light image and the P-polarized light image are stored in the image memories 72a and 72b, respectively. The calculation processing unit 73 calculates a reflectance difference based on brightness of the S-polarized light image and that of the P-polarized light image stored in the image memories 72a and 72b. At this time, as the brightness of the S-polarized light image stored in the image memory 72a is reduced, and the reflectance difference $\Delta R$ between the S-polarized light and the P-polarized light becomes small. The calculation processing unit 73 outputs this calculation result to the raindrop determination unit 74. When the reflectance difference $\Delta R$ between the S-polarized light and the P-polarized light from the calculation processing unit 73 becomes small, the raindrop determination unit 74 determines that it has started raining. Then, when the reflectance difference $\Delta R$ between the S-polarized light and the P-polarized light reaches a specified value $\Delta Rt$, e.g., $\Delta Rt=(80-20)$, the raindrop determination unit 74 outputs a driving signal for driving a wiper of a vehicle to the driving control unit 7.

Thus, the raindrop detection apparatus can determine the presence or absence of raindrops 200 on the windshield 100, and if present, reliably detect an amount of the raindrops with a simple configuration.

Figure 21:
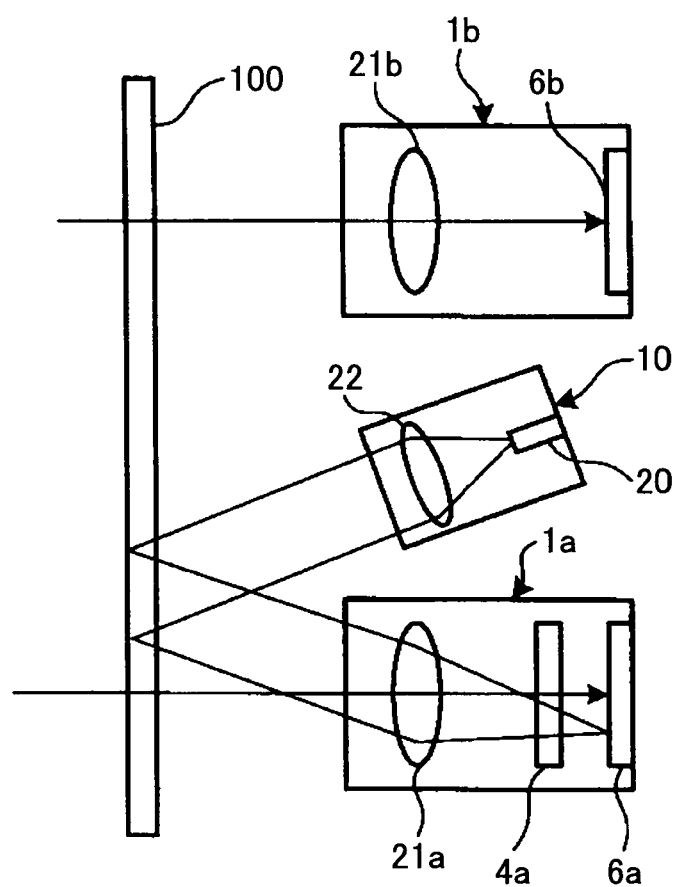
FIG. 21 is a configuration diagram of a first optical system of an on-vehicle monitoring apparatus.
Figure 22:
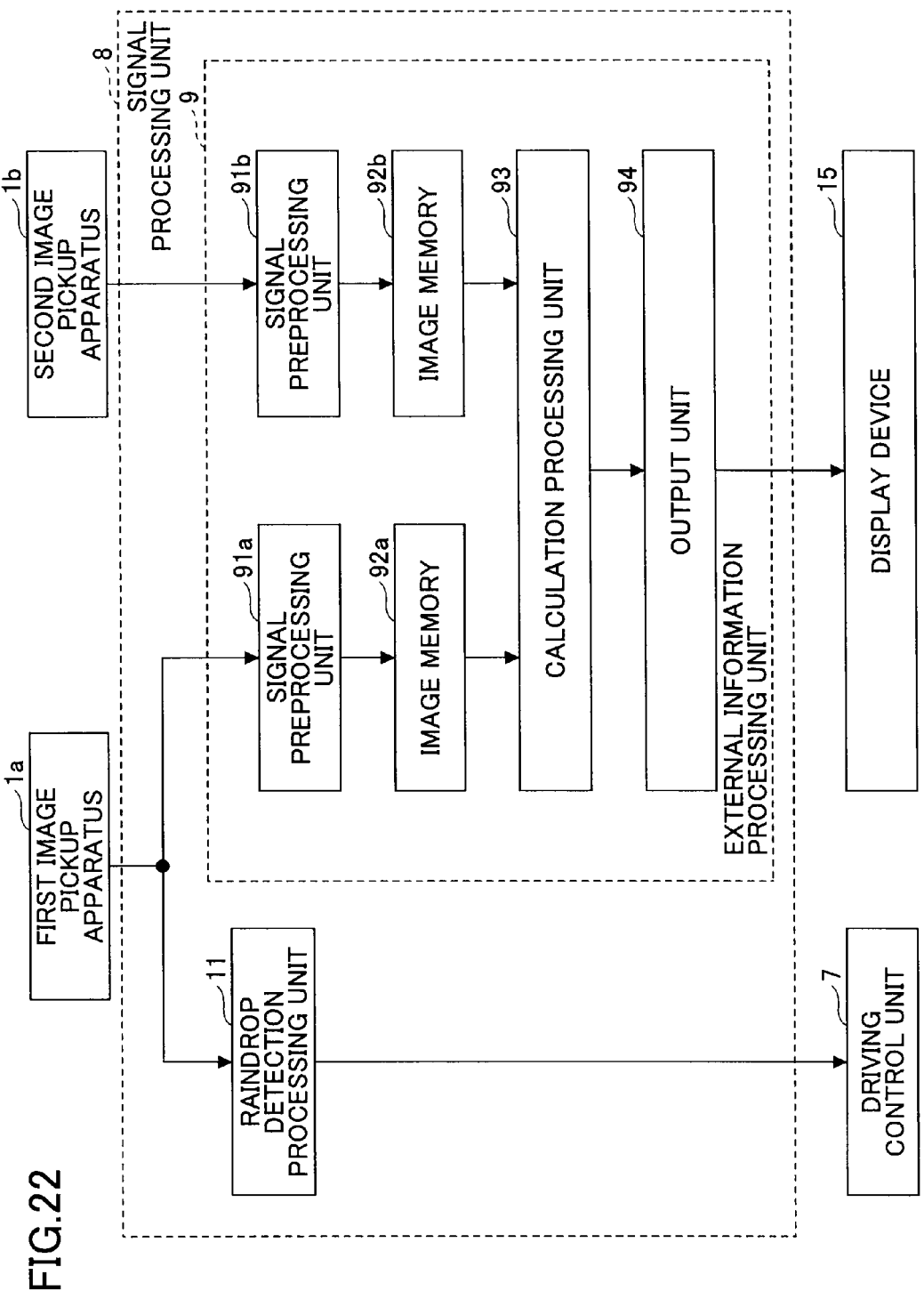
FIG. 22 is a block diagram showing the configuration of a signal processing unit of the on-vehicle monitoring apparatus.

Referring next to a configuration diagram showing an optical system in FIG. 21 and a block diagram showing the configuration of a signal processing unit 8 in FIG. 22, a description is made of an on-vehicle monitoring apparatus that has the raindrop detection apparatus described above and monitors the front side of a vehicle.

The optical system of the on-vehicle monitoring apparatus has a first image pickup apparatus 1a, a second image pickup apparatus 1b, and a light source 10, and is provided near the rearview mirror of a vehicle. The first image pickup apparatus 1a receives the light, which is applied from the light source 10 to the windshield 100 and reflected by the windshield 100, to pick up an S-polarized image and a P-polarized image. In addition, the first image pickup apparatus 1a picks up images of vehicles, persons, obstacles, or the like ahead of the vehicle in common with the second image pickup apparatus 1b. The light source 10 has a light-emitting device 20 such as a LED and a lens 22. The light source 10 converts light emitted from the light-emitting device 20 into parallel light flux and irradiates the windshield 100 with the light at Brewster's angle $\theta B$.

Figure 23A:
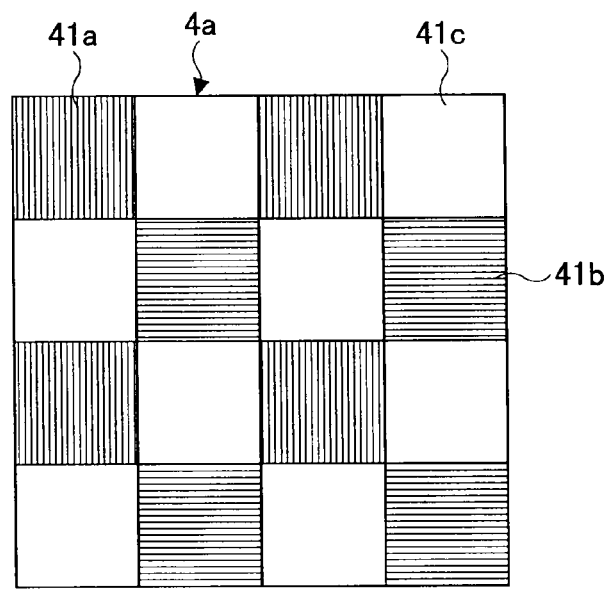
FIGS. 23A and 23B are plan views showing the configuration of a polarized light filter and a solid-state image pickup unit used in an image pickup apparatus of the on-vehicle monitoring apparatus.
Figure 23B:
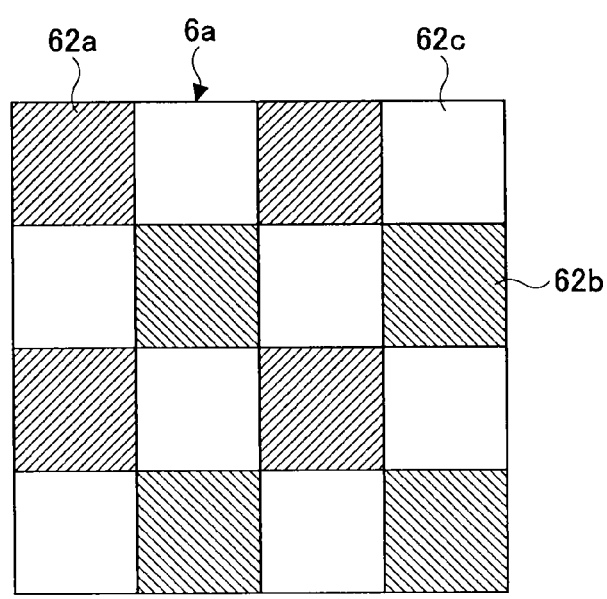

The first image pickup apparatus 1a is composed of an image pickup lens 21a, a polarized light filter 4a, and a solid-state image pickup unit 6a. As shown in FIG. 23A, the polarized light filter 4a has plural polarizer regions 41a that allow only the light of an S-polarized light component to pass through, plural polarizer regions 41b that allow only the light of a P-polarized light component to pass through, and plural non-polarizer regions 41c that do not separate polarized light. As shown in FIG. 23B, the solid-state image pickup unit 6a has plural first image pickup devices 62a, second image pickup devices 62b, and third image pickup devices 62c on a substrate 61 so as to correspond to the polarizer regions 41a, the polarizer regions 41b, and the non-polarizer regions 41c of the polarized light filter 4a. The second image pickup apparatus 1b is composed of an image pickup lens 21b and a solid-state image pickup unit 6b. The image pickup lens 21a of the first image pickup apparatus 1a and the image pickup lens 21b of the second image pickup apparatus 1b focus on an object several to tens of meters ahead.

As shown in the block diagram in FIG. 22, the signal processing unit 8 of the on-vehicle monitoring apparatus has the raindrop detection processing unit 11 and an external information processing unit 9. The external information processing unit 9 has signal preprocessing units 91a and 91b, image memories 92a and 92b, a distance calculation processing unit 93, and an output unit 94. The signal preprocessing units 91a and 91b perform shading correction or the like for correcting the sensitivity unevenness or the like of image signals output from the first image pickup apparatus 1a and the second image pickup apparatus 1b and store information pertaining to ahead of the vehicle, i.e., images of vehicles, persons, and white lines on the road ahead of the vehicle in the image memories 92a and 92b. The distance calculation processing unit 93 calculates a distance to an in-front vehicle or the like based on the parallax of the images stored in the image memories 92a and 92b. The output unit 94 outputs the distance calculated by the distance calculation processing unit 93 and the image of the in-front vehicle or the like to the display device 15 so as to be displayed. Furthermore, when a distance to the in-front vehicle or the like is short, the output unit 94 may automatically output a signal for operating a brake to sound an alarm in order to avoid collision with the front vehicle or the like.

Here, a description is made of processing when the first image pickup apparatus 1a and the second image pickup apparatus 1b of the on-vehicle monitoring apparatus pick up the image of an in-front vehicle or the like and the signal processing unit 8 calculates a distance to the in-front vehicle or the like based on the picked up image.

Figure 24:
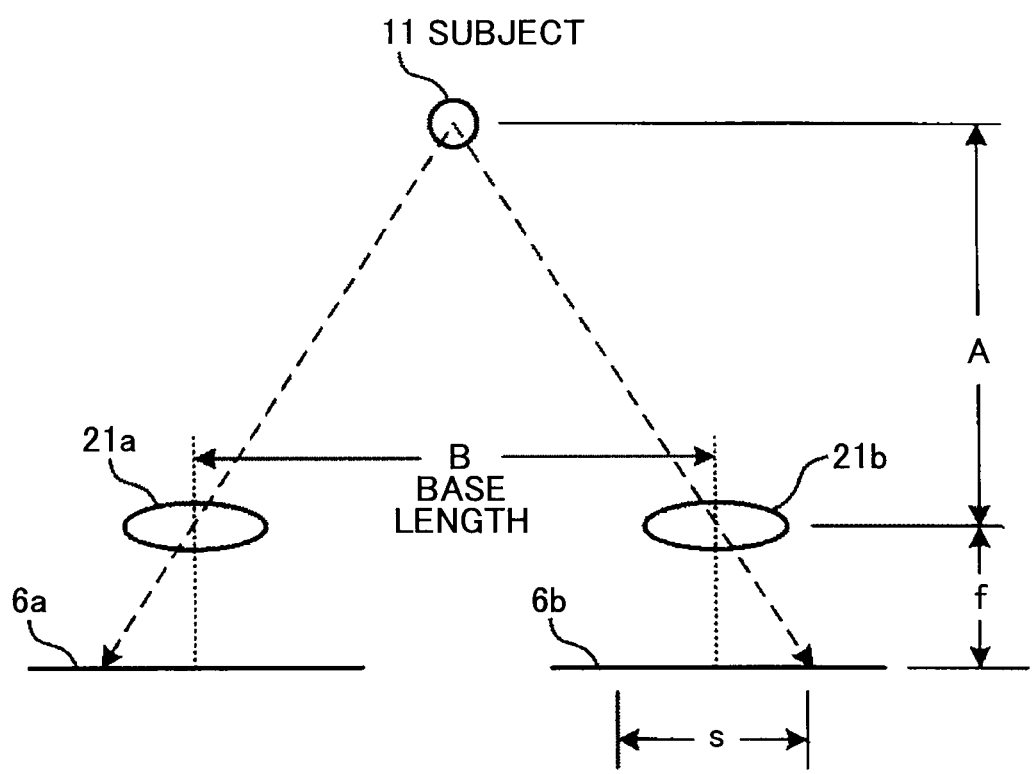
FIG. 24 is a schematic view showing processing for calculating a distance to an ahead subject.

When the first image pickup apparatus 1a picks up an image of a front vehicle or the like, it causes light incident from the image pickup lens 21a to pass through the polarizer regions 41a, the polarizer regions 41b, and non-polarizer regions 41c of the polarized light filter 4a and be received by the first image pickup devices 62a, the second image pickup devices 62b, and the third image pickup devices 62c of the solid-state image pickup unit 6a. Furthermore, the second image pickup apparatus 1b also receives light incident from the image pickup lens 21b at the solid-state image pickup unit 6b to pick up an image of the in-front vehicle or the like. The images picked up by the first image pickup apparatus 1a and the second image pickup apparatus 1b are input to the signal preprocessing units 91a and 91b of the signal processing unit 8 for preprocessing and stored in the image memories 92a and 92b, respectively. The distance calculation processing unit 93 reads the images stored in the image memories 92a and 92b and calculates a distance to the in-front vehicle or the like based on the principle of triangular surveying. As shown in a schematic diagram in FIG. 24, when it is assumed that a focal distance of the image pickup lens 21a of the first image pickup apparatus 1a and the image pickup lens 21b of the second image pickup apparatus 1b is defined as "f," an interval (base length) between the image pickup lenses 21a and 21b is defined as "B," a distance to a subject 11 is defined as "A," and a pixel size of the respective image pickup devices of the solid-state image pickup units 6a and 6b is defined as "δ" so as to calculate the distance to the subject 11 such as an in-front vehicle or the like, the parallax S of the images picked up by the first image pickup apparatus 1a and the second image pickup apparatus 1b is expressed by the following formula (1).

$$S = (B \cdot f)/(A \cdot \delta) \quad (1)$$

Thus, the distance A to the subject 11 can be calculated based on the parallax S of the images picked up by the first image pickup apparatus 1a and the second image pickup apparatus 1b. The larger the parallax S is, the easier the calculation of the distance A to the subject 11 can be made. Therefore, in order to measure a long distance, the focal distance f of the image pickup lenses 21a and 21b and the interval (base length) B between the image pickup lenses 21a and 21b may be set large.

Furthermore, when the on-vehicle monitoring apparatus determines the presence or absence of raindrops 200 on the windshield 100, the first image pickup apparatus 1a picks up light emitted from the light source 10 and reflected by the windshield 100 and the raindrop detection processing unit 11 processes the picked up S-polarized light image and P-polarized light image.

Figure 25:
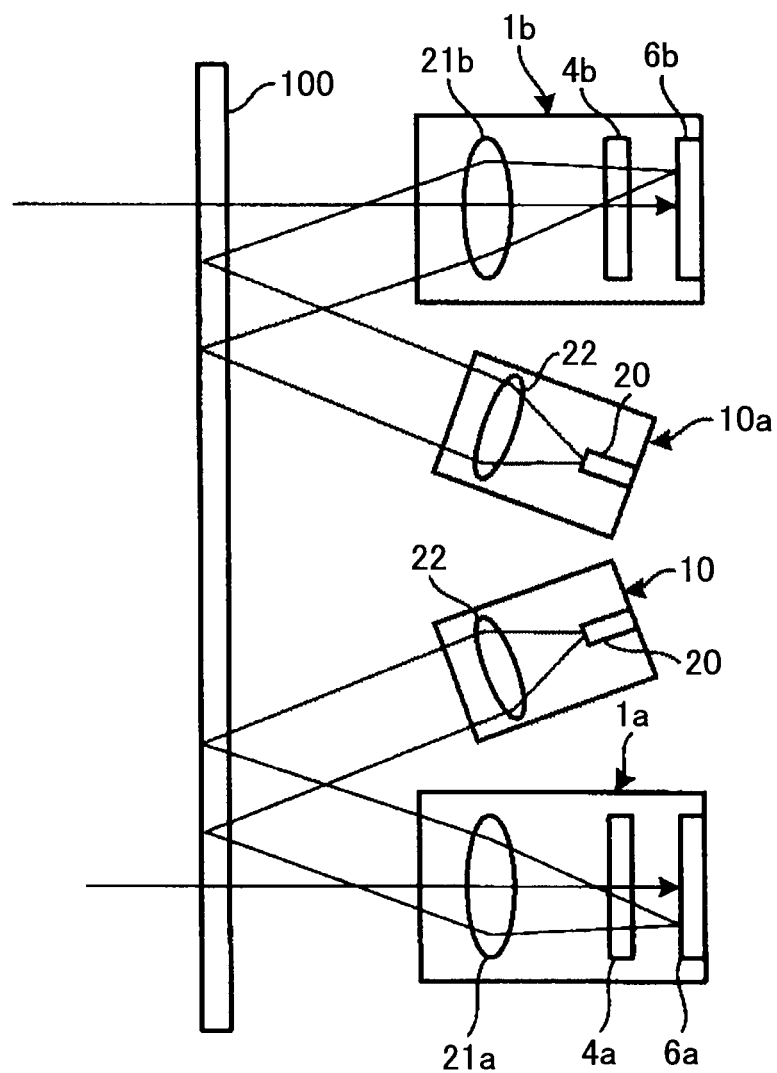
FIG. 25 is a configuration diagram of a second optical system of the on-vehicle monitoring apparatus.

In the above description, the on-vehicle monitoring apparatus determines the presence of raindrops 200 on the windshield 100 in such a manner that the first image pickup apparatus 1a picks up the light emitted from the light source 10 and reflected by the windshield 100. However, as shown in a configuration diagram in FIG. 25, the optical system may be arranged such that the second image pickup apparatus 1b has the same configuration as that of the first image pickup apparatus 1a and a second light source 10a is provided. With this arrangement, the second image pickup apparatus 1b picks up the light emitted from the second light source 10a and reflected by the windshield 100, and the raindrop detection processing unit 11 processes the picked up S-polarized light image and P-polarized light image, thereby determining the presence or absence of raindrops 200 on the windshield 100. Thus, the presence or absence of raindrops 200 on the windshield 100 is determined based on the images of the windshield 100 picked up by the first image pickup apparatus 1a and the second image pickup apparatus 1b. Accordingly, the presence or absence of raindrops 200 on the windshield 100 is determined in a larger area, thereby making possible detecting the raindrops 200 attached to the windshield 100 and an amount of the raindrops 200 with high accuracy.

Figure 26:
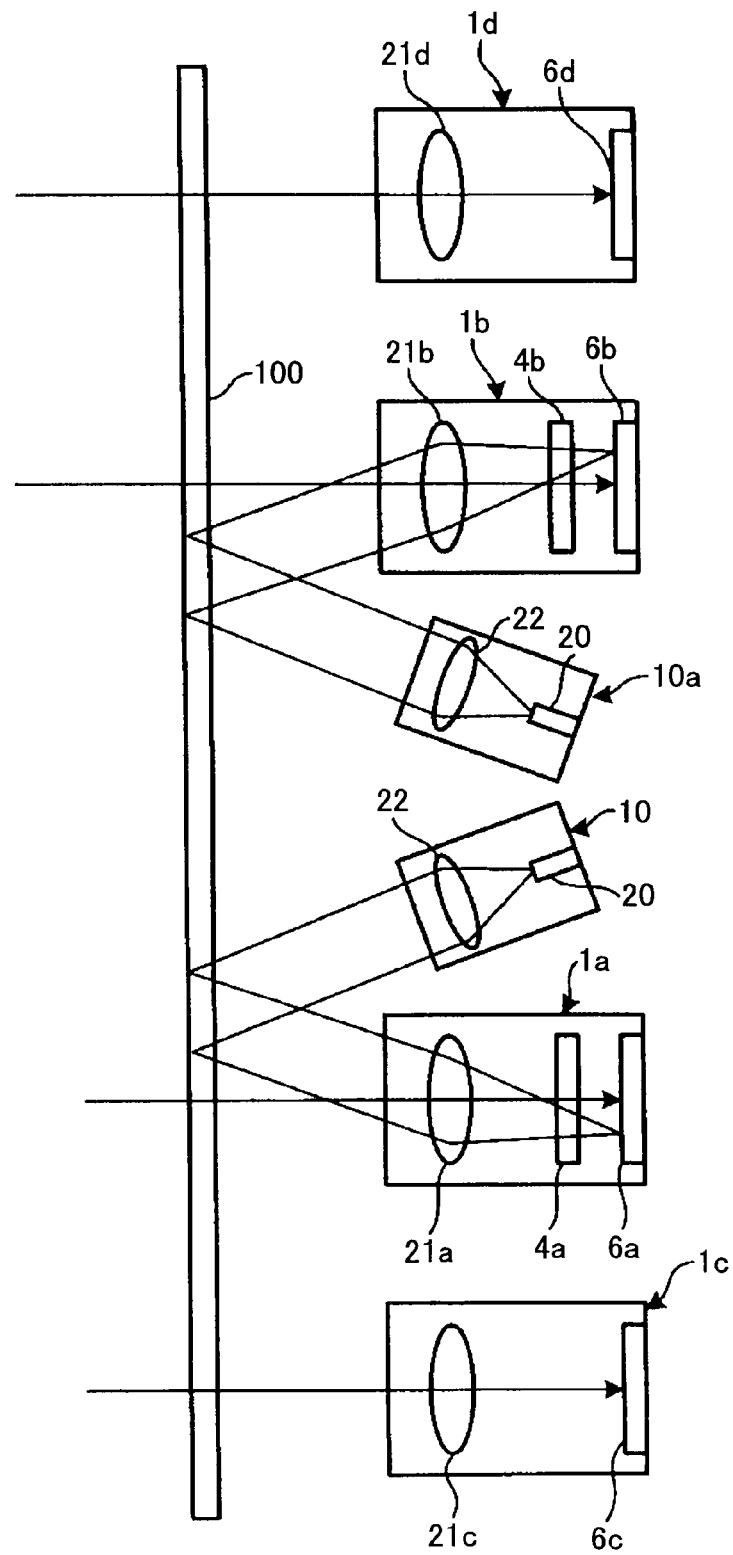
FIG. 26 is a configuration diagram of a third optical system of the on-vehicle monitoring apparatus.

Furthermore, as shown in a configuration diagram in FIG. 26, the optical system may be arranged such that a third image pickup apparatus 1c and a fourth image pickup apparatus 1d are provided besides the first image pickup apparatus 1a and the second image pickup apparatus 1b. In this case, each of the image pickup lens 21a of the first image pickup apparatus 1a and the image pickup lens 21b of the second image pickup apparatus 1b may have a short focal distance for measuring a short distance, while each of the image pickup lens 21c of the third image pickup apparatus 1c and the image pickup lens 21d of the fourth image pickup apparatus 1d may have a long focal distance for measuring a long distance.

With the provision of the first and second image pickup apparatuses 1a and 1b for measuring a short distance and the third and fourth image pickup apparatuses 1c and 1d for measuring a long distance, the on-vehicle monitoring apparatus can detect a distance to an in-front vehicle or the like with high accuracy ranging widely from a short distance to a long distance, perform wide-angle detection in a short distance, and reliably detect subjects 11 rushing toward the vehicle from left and right side of the vehicle.

In the above description, the polarizer regions 41a and 41b of the polarized light filters 4 and 4a are made of photonic crystal. However, as the polarizer regions 41a and 41b, wire grid type polarizers may be used. The wire grid type polarizers are made of periodically-arranged thin metal wire, which have been conventionally used in the millimeter wave region of electromagnetic waves in many cases. The wire grid type polarizers have a structure in which thin metal wires substantially smaller than the wavelength of input light are arranged at intervals substantially smaller than the wavelength. It is known that, when light is applied to such a structure, polarized light parallel to the metal thin wires is reflected by the wire grid type polarizers while polarized light orthogonal to the metal thin wires passes through the wire grid type polarizers. Since the direction of the metal thin wires can be made different according to regions in a single substrate, the characteristics of the wire grid type polarizers can be changed according to the regions. Thus, the polarized light filters 4 and 4a may be arranged such that the direction of a transmission axis is changed according to the polarizer regions 41a and 41b.

As a method for manufacturing wire grids, a metal film is formed on a substrate and then patterned by lithography. Thus, thin wire-like metal parts can be formed on the substrate. Another method for manufacturing wire grids is to form grooves in a substrate by lithography and deposit metal on the substrate by vacuum deposition from the direction (diagonal direction against the surface of the substrate) that is perpendicular to the direction of the grooves and inclined from the normal line the substrate. In vacuum deposition, since particles coming out from a deposition source hardly collide with other molecules or atoms on their way and particles linearly move from the deposition source to the substrate, a film is deposited only at convex parts forming the grooves while almost no film is formed at the bottom parts (concave parts) of the grooves because the particles are blocked by the convex parts. Accordingly, a metal film can be deposited only at the convex parts of the grooves on the substrate by controlling a film deposition amount. As a result, metal thin wires can be manufactured. As wire metal used for the wire grid type polarizers, aluminum or copper may be preferred. However, other metals such as tungsten can achieve a similar phenomenon. Furthermore, examples of lithography include optical lithography, electron beam lithography, X-ray lithography, or the like. Since an interval between thin wires is about 100 nm when operations with visible light are taken into consideration, electron beam lithography or X-ray lithography are more preferred. Furthermore, vacuum deposition is preferred when a film is deposited with metal. However, since the direction of particles incident on a substrate is mainly significant, sputtering in a high vacuum atmosphere or collimation sputtering using a collimator are available.

The present invention is not limited to the specifically disclosed embodiments, and variations and modifications may be made without departing from the scope of the present invention.

The present application is based on Japanese Priority Applications No. 2009-032161 filed on Feb. 16, 2009, No. 2009-052761 filed on Mar. 6, 2009, and No. 2009-204319 filed on Sep. 4, 2009, the entire contents of which are hereby incorporated herein by reference.

What is claimed is:

1. A liquid droplet recognition apparatus for detecting a liquid droplet attached to a front surface of a transparent member, the apparatus comprising:
   an image pickup apparatus that picks up a vertically polarized light image and a horizontally polarized light image at the front surface of the transparent member from a side of a rear surface of the transparent member; and
   a signal processing unit that determines whether the liquid droplet is attached to the front surface of the transparent member based on a polarized-light image ratio composed of the vertically polarized light image and the horizontally polarized light image picked up by the image pickup apparatus,
   wherein the image pickup apparatus includes
      a lens array having a plurality of image pickup lenses on a same substrate,
      a filter that is separated into two polarizer regions with transmission axes orthogonal to each other so as to correspond to light fluxes passing through the plurality of image pickup lenses of the lens array, and
      an image pickup unit having a plurality of image pickup regions that pick up an image of a subject by receiving light passing through the respective polarizer regions of the filter,
   wherein the vertically polarized light image is picked up by any of the plurality of image pickup regions of the image pickup unit and the horizontally polarized light image is picked up by another of the plurality of image pickup regions thereof, and
   wherein the signal processing unit includes an image position correction unit that corrects a parallax positional shift between the vertically polarized light image and the horizontally polarized light image picked up by the plurality of image pickup regions.

2. The liquid droplet recognition apparatus according to claim 1, wherein the image pickup apparatus further comprises:
   a beam splitter that separates a light flux passing through the plurality of image pickup lenses into two parallel light fluxes,
   wherein the transmission axes that are orthogonal to each other correspond to the two parallel light fluxes separated by the beam splitter, and
   wherein the vertically polarized light image is acquired by the light flux passing through one of the two polarizer regions of the filter and the horizontally polarized light image is acquired by the light flux passing through the other of the two polarizer regions thereof.

3. The liquid droplet recognition apparatus according to claim 1 wherein the two polarizer regions of the filter have a multilayer structure in which a plurality of transparent materials with different refractive indexes are laminated together on a transparent substrate and have one-dimensional periodic irregularities repeatedly formed in one direction for the layers.

4. A raindrop recognition apparatus using the liquid droplet recognition apparatus according to claim 1, wherein the image pickup apparatus is provided inside a vehicle and detects a raindrop attached to a front surface of a windshield of the vehicle.

5. The raindrop recognition apparatus according to claim 4, further comprising:
   a light source that irradiates a region of the windshield of the vehicle with illumination light of a wavelength range not visible to a human eye to be picked up by the image pickup apparatus.

6. An on-vehicle monitoring apparatus comprising:
   a first light source;
   first and second image pickup apparatuses; and
   a signal processing unit;
   wherein the light source, the first and second image pickup apparatuses, and the signal processing unit are mounted on a vehicle,
   wherein the light source irradiates a windshield of the vehicle with a parallel light flux at an incident angle of Brewster's angle,
   wherein the first image pickup apparatuses picks up an S-polarized light image and a P-polarized light image by receiving reflection light of the light flux irradiated from the light source to the windshield while picking up an image of a subject ahead of the vehicle,
   wherein the second image pickup apparatuses picks up an image of the subject ahead of the vehicle, and
   wherein the signal processing unit has a raindrop detection processing unit and an external information processing unit, the raindrop detection processing unit determining whether a raindrop is attached to the windshield based on a reflectance difference between the S-polarized light image and the P-polarized light image picked up by the first image pickup apparatus and the external information processing unit calculating a distance to the subject based on the images of the subject ahead of the vehicle picked up by the first image pickup apparatus and the second image pickup apparatus, wherein the first image pickup apparatus includes
a lens array having a plurality of image pickup lenses on a same substrate,
a filter that is separated into two polarizer regions with transmission axes orthogonal to each other so as to correspond to light fluxes passing through the plurality of image pickup lenses of the lens array, and
an image pickup unit having a plurality of image pickup regions that pick up an image of a subject by receiving light passing through the respective polarizer regions of the filter,
wherein a vertically polarized light image is picked up by any of the plurality of image pickup regions of the image pickup unit and the horizontally polarized light image is picked up by another of the plurity of image pickup regions thereof, and
wherein the signal processing unit includes an image position correction unit that corrects a parallax positional shift between the vertically polarized light image and the horizontally polarized light image picked up by the plurality of image pickup regions.

7. The on-vehicle monitoring apparatus according to claim 6, wherein the filter of the first image pickup apparatus is a polarized light filter that is provided on an outgoing side of the light flux passing through the plurality of image pickup lenses and the two polarizer regions where polarized light is separated by transmission axes orthogonal to each other and a region where the polarized light is not separated,
wherein the image of the subject picked up by the image pick up unit is an image of a front surface of the windshield, and
wherein the first image pickup apparatus acquires the S-polarized light image from the light flux passing through a first of the two polarizer regions of the polarized light filter and acquires the P-polarized light image from the light flux passing through a second of the two polarizer regions thereof.

8. The on-vehicle monitoring apparatus according to claim 6, further comprising:
a second light source,
wherein the first light source and the second light source irradiate different regions of the windshield of the vehicle with parallel light fluxes at an incident angle of Brewster's angle,
wherein the first and second of image pickup apparatuses pick up S-polarized light images and P-polarized light images by receiving reflection light of the light fluxes irradiated from the first and second light sources to the different regions of the windshield while picking up images of the subject ahead of the vehicle, and
wherein the raindrop detection processing unit of the signal processing unit determines whether a raindrop is attached to the windshield based on a reflectance difference between the S-polarized light images and the P-polarized light images picked up by the first and second image pickup apparatuses.

9. The on-vehicle monitoring apparatus according to claim 6, further comprising:
third and fourth image pickup apparatuses, the first and second image pickup apparatuses being used for measuring a short distance and the third and fourth image pickup apparatuses being used for measuring a long distance;
wherein the external information processing unit of the signal processing unit calculates a distance to the subject based on the images of the subject ahead of the vehicle picked up by the first and second image pickup apparatuses for measuring the short distance and the third and fourth image pickup apparatuses for measuring the long distance.

10. The liquid droplet recognition apparatus according to claim 1, wherein the image pickup apparatus is disposed inside a vehicle to detect a raindrop attached to a front surface of a windshield of the vehicle, and
wherein the image pickup apparatus includes first and second polarizing regions, each region having grooves that extend in parallel with the surface of the windshield.

* * * * *